(12) United States Patent
Pastan et al.

(10) Patent No.: US 8,809,502 B2
(45) Date of Patent: *Aug. 19, 2014

(54) MUTATED ANTI-CD22 ANTIBODIES WITH INCREASED AFFINITY TO CD22-EXPRESSING LEUKEMIA CELLS

(75) Inventors: Ira Pastan, Potomac, MD (US); Giuliana Salvatore, Naples (IT); Richard Beers, Rockville, MD (US); Robert Kreitman, Potomac, MD (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 159 days.

This patent is subject to a terminal disclaimer.

(21) Appl. No.: 13/438,725

(22) Filed: Apr. 3, 2012

(65) Prior Publication Data

US 2012/0258106 A1 Oct. 11, 2012

Related U.S. Application Data

(60) Continuation of application No. 12/846,625, filed on Jul. 29, 2010, now abandoned, which is a continuation of application No. 12/030,828, filed on Feb. 13, 2008, now Pat. No. 7,777,019, which is a division of application No. 10/490,535, filed as application No. PCT/US02/30316 on Sep. 25, 2002, now Pat. No. 7,355,012.

(60) Provisional application No. 60/325,360, filed on Sep. 26, 2001.

(51) Int. Cl.
*A61K 39/00* (2006.01)

(52) U.S. Cl.
USPC .................................................. 530/387.1

(58) Field of Classification Search
None
See application file for complete search history.

(56) References Cited

U.S. PATENT DOCUMENTS

| 7,355,012 B2* | 4/2008 | Pastan et al. ............... 530/387.3 |
| 2006/0051349 A1 | 3/2006 | Goldenberg et al. |
| 2006/0057136 A1 | 3/2006 | Goldenberg |
| 2006/0194276 A1 | 8/2006 | Krauss et al. |
| 2007/0003556 A1 | 1/2007 | Tsuchiya et al. |
| 2007/0059307 A1 | 3/2007 | Popplewell et al. |

FOREIGN PATENT DOCUMENTS

| WO | WO/98/41641 | * | 9/1998 | ............. C12N 15/70 |
| WO | WO03/104425 A2 | | 12/2003 | |

OTHER PUBLICATIONS

Chowdhury, Partha S. et al.; "Improving antibody affinity by mimicking hypermutation in vitro"; 1999, *Nature Biotechnology*, vol. 17, pp. 568-572.

Frankel, Arthur E.; "Increased Sophistication of Immunotoxins"; 2002, *Clinical Cancer Research*, vol. 8, pp. 942-944.

Kreitman, Robert J. et al.; "Complete Regression of Human B-Cell Lymphoma Xenografts in Mice Treated with Recombinant Anti-CD22 Immunotoxin RFB4(dsFv)-PE38 at Doses Tolerated by Cynomolgus Monkeys"; 1999, *International Journal of Cancer*, vol. 81, pp. 148-155.

Kreitman, Robert J. et al.; "Cytotoxic Activity of Disulfide-stabilized Recombinant Immunotoxin RFB4(dsFv)-PE38 (BL22) toward Fresh Malignant Cells from Patients with B-Cell Leukemias"; 2000, *Clinical Cancer Research*, vol. 6, pp. 1476-1487.

Kreitman, Robert J. et al.; "Efficacy of the Anti-CD22 Recombinant Immunotoxin BL22 in Chemotherapy-Resistant Hairy-Cell Leukemia"; 2001, *New England Journal of Medicine*, vol. 345, No. 4, pp. 241-247.

Mansfield, Elizabeth et al.; "Recombinant RFB4 single-chain immunotoxin that is cytotoxic towards CD22-positive cells"; 1997, *Biochem. Soc. Trans.*, vol. 25, pp. 709-714.

Mansfield, Elizabeth et al.; "Recombinant RFB4 Immunotoxins Exhibit Potent Cytotoxic Activity for CD22-Bearing Cells and Tumors"; 1997, *Blood*, vol. 90, pp. 2020-2026.

Salvatore, Giuliana et al.; "Improved Cytotoxic Activity toward Cell Lines and Fresh Leukemia Cells of a Mutant Anti-CD22 Immunotoxin Obtained by Antibody Phage Display";2002, *Clinical Cancer Research*, vol. 8, pp. 995-1002.

Short, M.K., et al., "A single H:CDR3 residue in the anti-digoxin antibody 26-10 modulates specificity for C16-substituted digoxin analogs," *Protein Engineering*, vol. 14(4), pp. 287-296 (2001).

Skolnick et al.; "From Genes to Protein Structure and Function; Novel Applications of Computational Approaches in the Genomic Era," *Trends in Biotechnology*, 2000, vol. 18, pp. 34-39.

Mac Callum, et al.; "Antibody-Antigen Interactions: Contact Analysis and Binding Site Topography," *Journal of Molecular Biology*, 1996, vol. 262, pp. 732-745.

De Pascalis et al.; "Grafting of Abbreviated Complementarity Determining Regions Containing Specificity Determining Residues Essential for Ligand Contact to Engineer a Less Immunogenic Humanized Monoclonal Antibody," *Journal of Immunology*, 2002. vol. 169, pp. 3076-3084.

(Continued)

*Primary Examiner* — Brad Duffy
*Assistant Examiner* — Nelson B Moseley, III
(74) *Attorney, Agent, or Firm* — Kilpatrick Townsend & Stockton LLP

(57) ABSTRACT

Recombinant immunotoxins are fusion proteins composed of the Fv domains of antibodies fused to bacterial or plant toxins. RFB4 (Fv)-PE38 is an immunotoxin that targets CD22 expressed on B cells and B cell malignancies. The present invention provides antibodies and antibody fragments that have improved ability to bind the CD22 antigen of B cells and B cell malignancies compared to RFB4. Immunotoxins made with the antibodies and antibody fragments of the invention have improved cytotoxicity to CD22-expressing cancer cells. Compositions that incorporate these antibodies into chimeric immunotoxin molecules that can be used in medicaments and methods for inhibiting the growth and proliferation of leukemia and lymphoma cells.

18 Claims, 3 Drawing Sheets

(56) References Cited

OTHER PUBLICATIONS

Casset et al.; "A Peptide Mimetic of an Anti-CD4 Monoclonal Antibody by Rational Design," *Biochemical and Biophysical Research Communications*, 2003. vol. 307, pp. 198-205.

Holm et al.; "Functional Mapping and Single Chain Construction of the Anti-Cytokeratin 8 Monoclonal Antibody TS1," *Molecular Immunology*, 2007, vol. 44, pp. 1075-1084.

Chen et al.; "Selection and Analysis of an Optimized Anti-VEGF Antobody: Crystal Structure of an Affinity Matured Fab in Complex with Antigen," Journal of Molecular Biology. 1999, vol. 293, pp. 865-881.

Wu, et al.; "Humanization of a Murine Monoclonal Antibody by Simultaneous Optimization of Framework and CDR Residues," *Journal of Molecular Biology*, 1999, vol. 294, pp. 151-162.

\* cited by examiner

RFB4 LIGHT CHAIN

```
  1   D   I   Q   M   T   Q   T   S   S   L   S   A   S   L   G   D   R   V   T    20
  1  gat atc cag atg acc cag act tcc tcc ctg tct gcc tct ctg gga gac aga gtc acc    60

21   I   S   C   R   A   S   Q   D   I   S   N   Y   L   N   W   Y   Q   Q   K   P    40
 61  att agt tgc aga gca agt cag gac att agc aat tat tta aac tgg tat cag cag aaa cca  120

41   D   G   T   V   K   L   L   I   Y   Y   T   S   I   L   H   S   G   V   P   S    60
121  gat gga act gtt aaa ctc ctg atc tac tac aca tca ata tta cac tca gga gtc cca tca  180

61   R   F   S   G   S   G   S   G   T   D   Y   S   L   T   I   S   N   L   E   Q    80
181  agg ttc agt ggc agt ggg tct gga aca gat tat tct ctc acc att agc aac ctg gag caa  240

81   E   D   F   A   T   Y   F   C   Q   Q   G   N   T   L   P   W   T   F   G   G   100
241  gaa gat ttt gcc act tac ttc tgc caa caa ggt aat acg ctt ccg tgg acg ttc ggt gga  300

101   G   T   K   L   E   I   K                                                       107
301  gga acc aag ctg gaa atc aaa                                                       121
```

RFB4 HEAVY CHAIN

```
  1   E   V   Q   L   V   E   S   G   G   G   L   V   K   P   G   G   S   L   K   L    20
  1  gaa gtg cag ctg gtg gag tct ggg gga ggc tta gtg aag cct gga ggg tcc ctg aaa ctc   60

21   S   C   A   A   S   G   F   A   F   S   I   Y   D   M   S   W   V   R   Q   T    40
 61  tcc tgt gca gcc tct gga ttc gct ttc agt atc tat gac atg tct tgg gtt cgc cag act  120

41   P   E   K   R   L   E   W   V   A   Y   I   S   S   G   G   G   T   T   Y   Y    60
121  ccg gag aag agg ctg gag tgg gtc gca tac att agt agt ggt ggt ggt acc acc tac tat  180

61   P   D   T   V   K   G   R   F   T   I   S   R   D   N   A   K   N   T   L   Y    80
181  cca gac act gtg aag ggc cga ttc acc atc tcc aga gac aat gcc aag aac acc ctg tac  240

81   L   Q   M   S   S   L   K   S   E   D   T   A   M   Y   Y   C   A   R   H   S   100
241  ctg caa atg agc agt ctg aag tct gag gac aca gcc atg tat tac tgt gca aga cat agt  300

101   G   Y   G   S   S   Y   G   V   L   F   A   Y   W   G   Q   G   T   L   V   T   120
301  ggc tac ggt agt agc tac ggg gtt ttg ttt gct tac tgg ggc caa ggg act ctg gtc act  360

121   V   S   A                                                                       123
361  gtc tct gca                                                                       369
```

FIG. 1

*Nucleotide/residue numbering shown first followed by Kabat Numbering*

| # | Kabat | Codon | AA3 | AA |
|---|---|---|---|---|
| 1 | 0 | --- | --- | - |
| 2 | 1 | gat | ASP | D |
| 3 | 2 | atc | ILE | I |
| 4 | 3 | cag | GLN | Q |
| 5 | 4 | atg | MET | M |
| 6 | 5 | acc | THR | T |
| 7 | 6 | cag | GLN | Q |
| 8 | 7 | act | THR | T |
| 9 | 8 | aca | THR | T |
| 10 | 9 | tcc | SER | S |
| 11 | 10 | tcc | SER | S |
| 12 | 11 | ctg | LEU | L |
| 13 | 12 | tct | SER | S |
| 14 | 13 | gcc | ALA | A |
| 15 | 14 | tct | SER | S |
| 16 | 15 | ctg | LEU | L |
| 17 | 16 | gga | GLY | G |
| 18 | 17 | gac | ASP | D |
| 19 | 18 | aga | ARG | R |
| 20 | 19 | gtc | VAL | V |
| 21 | 20 | acc | THR | T |
| 22 | 21 | att | ILE | I |
| 23 | 22 | agt | SER | S |
| 24 | 23 | tgc | CYS | C |
| 25 | 24 | agg | ARG | R |
| 26 | 25 | gca | ALA | A |
| 27 | 26 | agt | SER | S |
| 28 | 27 | cag | GLN | Q |
| 29 | 27A | --- | --- | - |
| 30 | 27B | --- | --- | - |
| 31 | 27C | --- | --- | - |
| 32 | 27D | --- | --- | - |
| 33 | 27E | --- | --- | - |
| 34 | 27F | --- | --- | - |
| 35 | 28 | gac | ASP | D |
| 36 | 29 | att | ILE | I |
| 37 | 30 | agc | SER | S |
| 38 | 31 | aat | ASN | N |
| 39 | 32 | tat | TYR | Y |
| 40 | 33 | tta | LEU | L |
| 41 | 34 | aac | ASN | N |
| 42 | 35 | tgg | TRP | W |
| 43 | 36 | tat | TYR | Y |
| 44 | 37 | cag | GLN | Q |
| 45 | 38 | cag | GLN | Q |
| 46 | 39 | aaa | LYS | K |
| 47 | 40 | cca | PRO | P |
| 48 | 41 | gat | ASP | D |
| 49 | 42 | gga | GLY | G |
| 50 | 43 | act | THR | T |
| 51 | 44 | gtt | VAL | V |
| 52 | 45 | aaa | LYS | K |
| 53 | 46 | ctc | LEU | L |
| 54 | 47 | ctg | LEU | L |
| 55 | 48 | atc | ILE | I |
| 56 | 49 | tac | TYR | Y |
| 57 | 50 | tac | TYR | Y |
| 58 | 51 | aca | THR | T |
| 59 | 52 | tca | SER | S |
| 60 | 53 | ata | ILE | I |
| 61 | 54 | tta | LEU | L |
| 62 | 55 | cac | HIS | H |
| 63 | 56 | tca | SER | S |
| 64 | 57 | gga | GLY | G |
| 65 | 58 | gtc | VAL | V |
| 66 | 59 | cca | PRO | P |
| 67 | 60 | tca | SER | S |
| 68 | 61 | agg | ARG | R |
| 69 | 62 | ttc | PHE | F |
| 70 | 63 | agt | SER | S |
| 71 | 64 | ggc | GLY | G |
| 72 | 65 | agt | SER | S |
| 73 | 66 | ggg | GLY | G |
| 74 | 67 | tct | SER | S |
| 75 | 68 | gga | GLY | G |
| 76 | 69 | aca | THR | T |
| 77 | 70 | gat | ASP | D |
| 78 | 71 | tat | TYR | Y |
| 79 | 72 | tct | SER | S |
| 80 | 73 | ctc | LEU | L |
| 81 | 74 | acc | THR | T |
| 82 | 75 | att | ILE | I |
| 83 | 76 | agc | SER | S |
| 84 | 77 | aac | ASN | N |
| 85 | 78 | ctg | LEU | L |
| 86 | 79 | gag | GLU | E |
| 87 | 80 | caa | GLN | Q |
| 88 | 81 | gaa | GLU | E |
| 89 | 82 | gat | ASP | D |
| 90 | 83 | ttt | PHE | F |
| 91 | 84 | gcc | ALA | A |
| 92 | 85 | act | THR | T |
| 93 | 86 | tac | TYR | Y |
| 94 | 87 | ttt | PHE | F |
| 95 | 88 | tgc | CYS | C |
| 96 | 89 | caa | GLN | Q |
| 97 | 90 | cag | GLN | Q |
| 98 | 91 | ggt | GLY | G |
| 99 | 92 | aat | ASN | N |
| 100 | 93 | acg | THR | T |
| 101 | 94 | ctt | LEU | L |
| 102 | 95 | ccg | PRO | P |
| 103 | 95A | --- | --- | - |
| 104 | 95B | --- | --- | - |
| 105 | 95C | --- | --- | - |
| 106 | 95D | --- | --- | - |
| 107 | 95E | --- | --- | - |
| 108 | 95F | --- | --- | - |
| 109 | 96 | tgg | TRP | W |
| 110 | 97 | acg | THR | T |
| 111 | 98 | ttc | PHE | F |
| 112 | 99 | ggt | GLY | G |
| 113 | 100 | gga | GLY | G |
| 114 | 101 | ggc | GLY | G |
| 115 | 102 | acc | THR | T |
| 116 | 103 | aag | LYS | K |
| 117 | 104 | ctg | LEU | L |
| 118 | 105 | gaa | GLU | E |
| 119 | 106 | atc | ILE | I |
| 120 | 106A | --- | --- | - |
| 121 | 107 | aaa | LYS | K |
| 122 | 108 | | | |
| 123 | 109 | | | |

*FIG. 2*

*Nucleotide/residue numbering shown first followed by Kabat Numbering*

| | | | | | | | | | | |
|---|---|---|---|---|---|---|---|---|---|---|
| 1 | 0 | --- | --- | - | 49 | 46 | gag | GLU | E |
| 2 | 1 | gaa | GLU | E | 50 | 47 | tgg | TRP | W |
| 3 | 2 | gtg | VAL | V | 51 | 48 | gtc | VAL | V |
| 4 | 3 | cag | GLN | Q | 52 | 49 | gca | ALA | A |
| 5 | 4 | ctg | LEU | L | 53 | 50 | tac | TYR | Y |
| 6 | 5 | gtg | VAL | V | 54 | 51 | att | ILE | I |
| 7 | 6 | gag | GLU | E | 55 | 52 | agt | SER | S |
| 8 | 7 | tct | SER | S | 56 | 52A | agt | SER | S |
| 9 | 8 | ggg | GLY | G | 57 | 52B | --- | --- | - |
| 10 | 9 | gga | GLY | G | 58 | 52C | --- | --- | - |
| 11 | 10 | ggc | GLY | G | 59 | 53 | ggt | GLY | G |
| 12 | 11 | tta | LEU | L | 60 | 54 | ggt | GLY | G |
| 13 | 12 | gtg | VAL | V | 61 | 55 | ggt | GLY | G |
| 14 | 13 | aag | LYS | K | 62 | 56 | acc | THR | T |
| 15 | 14 | cct | PRO | P | 63 | 57 | acc | THR | T |
| 16 | 15 | gga | GLY | G | 64 | 58 | tac | TYR | Y |
| | | | | | 65 | 59 | tat | TYR | Y |
| 17 | 16 | ggg | GLY | G | 66 | 60 | cca | PRO | P |
| 18 | 17 | tcc | SER | S | 67 | 61 | gac | ASP | D |
| 19 | 18 | ctg | LEU | L | 68 | 62 | act | THR | T |
| 20 | 19 | aaa | LYS | K | 69 | 63 | gtg | VAL | V |
| 21 | 20 | ctc | LEU | L | 70 | 64 | aag | LYS | K |
| 22 | 21 | tcc | SER | S | 71 | 65 | ggc | GLY | G |
| 23 | 22 | tgt | CYS | C | 72 | 66 | cga | ARG | R |
| 24 | 23 | gca | ALA | A | 73 | 67 | ttc | PHE | F |
| 25 | 24 | gcc | ALA | A | 74 | 68 | acc | THR | T |
| 26 | 25 | tct | SER | S | 75 | 69 | atc | ILE | I |
| 27 | 26 | gga | GLY | G | 76 | 70 | tcc | SER | S |
| 28 | 27 | ttc | PHE | F | 77 | 71 | aga | ARG | R |
| 29 | 28 | gct | ALA | A | 78 | 72 | gac | ASP | D |
| 30 | 29 | ttc | PHE | F | 79 | 73 | aat | ASN | N |
| 31 | 30 | agt | SER | S | 80 | 74 | gcc | ALA | A |
| 32 | 31 | atc | ILE | I | 81 | 75 | aag | LYS | K |
| 33 | 32 | tat | TYR | Y | 82 | 76 | aac | ASN | N |
| 34 | 33 | gac | ASP | D | 83 | 77 | acc | THR | T |
| 35 | 34 | atg | MET | M | 84 | 78 | ctg | LEU | L |
| 36 | 35 | tct | SER | S | | | | | |
| 37 | 35A | --- | --- | - | | | | | |
| 38 | 35B | --- | --- | - | | | | | |
| 39 | 36 | tgg | TRP | W | | | | | |
| 40 | 37 | gtt | VAL | V | | | | | |
| 41 | 38 | cgc | ARG | R | | | | | |
| 42 | 39 | cag | GLN | Q | | | | | |
| 43 | 40 | act | THR | T | | | | | |
| 44 | 41 | ccg | PRO | P | | | | | |
| 45 | 42 | gag | GLU | E | | | | | |
| 46 | 43 | aag | LYS | K | | | | | |
| 47 | 44 | agg | ARG | R | | | | | |
| 48 | 45 | ctg | LEU | L | | | | | |

| | | | | |
|---|---|---|---|---|
| 85 | 79 | tac | TYR | Y |
| 86 | 80 | ctg | LEU | L |
| 87 | 81 | caa | GLN | Q |
| 88 | 82 | atg | MET | M |
| 89 | 82A | agc | SER | S |
| 90 | 82B | agt | SER | S |
| 91 | 82C | ctg | LEU | L |
| 92 | 83 | aag | LYS | K |
| 93 | 84 | tct | SER | S |
| 94 | 85 | gag | GLU | E |
| 95 | 86 | gac | ASP | D |
| 96 | 87 | aca | THR | T |
| 97 | 88 | gcc | ALA | A |
| 98 | 89 | atg | MET | M |
| 99 | 90 | tat | TYR | Y |
| 100 | 91 | tac | TYR | Y |
| 101 | 92 | tgt | CYS | C |
| 102 | 93 | gca | ALA | A |
| 103 | 94 | aga | ARG | R |
| 104 | 95 | cat | HIS | H |
| 105 | 96 | agt | SER | S |
| 106 | 97 | ggc | GLY | G |
| 107 | 98 | tac | TYR | Y |
| 108 | 99 | ggt | GLY | G |
| 109 | 100 | agt | SER | S |
| 110 | 100A | agc | SER | S |
| 111 | 100B | tac | TYR | Y |
| 112 | 100C | ggg | GLY | G |
| 113 | 100D | gtt | VAL | V |
| 114 | 100E | ttg | LEU | L |
| 115 | 100F | --- | --- | - |
| 116 | 100G | --- | --- | - |
| 117 | 100H | --- | --- | - |
| 118 | 100I | --- | --- | - |
| 119 | 100J | --- | --- | - |
| 120 | 100K | ttt | PHE | F |
| 121 | 101 | gct | ALA | A |
| 122 | 102 | tac | TYR | Y |
| 123 | 103 | tgg | TRP | W |
| 124 | 104 | ggc | GLY | G |
| 125 | 105 | caa | GLN | Q |
| 126 | 106 | ggg | GLY | G |
| 127 | 107 | act | THR | T |
| 128 | 108 | ctg | LEU | L |
| 129 | 109 | gtc | VAL | V |
| 130 | 110 | act | THR | T |
| 131 | 111 | gtc | VAL | V |
| 132 | 112 | tct | SER | S |
| 133 | 113 | gca | ALA | A |

FIG. 3

MUTATED ANTI-CD22 ANTIBODIES WITH INCREASED AFFINITY TO CD22-EXPRESSING LEUKEMIA CELLS

CROSS-REFERENCES TO RELATED APPLICATIONS

This application is a continuation of U.S. application Ser. No. 12/846,625, filed Jul. 29, 2010, abandoned, which is a continuation of U.S. application Ser. No. 12/030,828, now U.S. Pat. No. 7,777,019, filed Feb. 13, 2008, which is divisional application of U.S. application Ser. No. 10/490,535, filed Mar. 23, 2004, now U.S. Pat. No. 7,355,012, which is a national stage application under 35 U.S.C. §371 of PCT/US02/30316, filed Sep. 22, 2002, which claimed priority from U.S. Provisional Application No. 60/325,360, filed Sep. 26, 2001. The contents of each of these disclosures is hereby incorporated by reference.

STATEMENT AS TO RIGHTS TO INVENTIONS MADE UNDER FEDERALLY SPONSORED RESEARCH OR DEVELOPMENT

Not applicable.

REFERENCE TO A "SEQUENCE LISTING," A TABLE, OR A COMPUTER PROGRAM LISTING APPENDIX SUBMITTED ON A COMPACT DISK

Not applicable.

BACKGROUND OF THE INVENTION

Hematological malignancies are a major public health problem. It has been estimated that in the year 2000, more than 50,000 new cases of non-Hodgkin's lymphoma and more than 30,000 new cases of leukemia occurred in the United States (Greenlee, R. T. et al., *CA Cancer J. Clin.,* 50:7-33 (2000)) and more than 45,000 deaths were expected from these diseases. Many more patients live with chronic disease-related morbidity. Unfortunately, in a high percentage of patients, conventional therapies are not able to induce long term complete remissions.

In the past several years immunotoxins have been developed as an alternative therapeutic approach to treat these malignancies. Immunotoxins were originally composed of an antibody chemically conjugated to a plant or a bacterial toxin. The antibody binds to the antigen expressed on the target cell and the toxin is internalized causing cell death by arresting protein synthesis and inducing apoptosis (Brinkmann, U., *Mol. Med. Today,* 2:439-446 (1996)).

Hematological malignancies are an attractive target for immunotoxin therapies because tumor cells are easily accessible and the target antigens are highly expressed (Kreitman, R. J. and Pastan, I., *Semin. Cancer Biol.,* 6:297-306 (1995)). One of these antigens is CD25. A clinical trial with immunotoxin LMB-2 (anti-Tac(Fv)-PE38) that targets CD25 showed that the agent was well tolerated and that it had substantial anti-tumor activity (Kreitman, R. J. et al., *Blood,* 94:3340-3348 (1999); Kreitman, R. J. et al., *J. Clin. Oncol.,* 18:16222-1636 (2000)). A complete response was observed in one patient with Hairy Cell Leukemia and partial responses were observed in patients with Hairy Cell Leukemia, chronic lymphocytic leukemia, cutaneous T cell lymphoma, Hodgkins disease and adult T cell leukemia.

Another antigen that has been used as an immunotoxin target is CD22, a lineage-restricted B cell antigen expressed in 60-70% of B cell lymphomas and leukemias. CD22 is not present on the cell surface in the early stages of B cell development and is not expressed on stem cells (Tedder, T. F. et al., *Annu. Rev. Immunol.,* 5:481-504 (1997)). Clinical trials have been conducted with an immunotoxin containing an anti-CD22 antibody, RFB4, or its Fab fragment, coupled to deglycosylated ricin A. In these trials, substantial clinical responses have been observed; however, severe and in certain cases fatal, vascular leak syndrome was dose limiting (Sausville, E. A. et al., *Blood,* 85:3457-3465 (1995); Amlot, P. L. et al., *Blood,* 82:2624-2633 (1993); Vitetta, E. S. et al., *Cancer Res.,* 51:4052-4058 (1991)).

As an alternative approach, the RFB4 antibody was used to make a recombinant immunotoxin in which the Fv fragment in a single chain form is fused to a 38 kDa truncated form of *Pseudomonas* exotoxin A (PE38). PE38 contains the translocating and ADP ribosylating domains of PE but not the cell-binding portion (Hwang, J. et al., *Cell,* 48:129-136 (1987)). RFB4 (Fv)-PE38 is cytotoxic towards CD22-positive cells (Mansfield, E. et al., *Biochem. Soc. Trans.,* 25:709-714 (1997)). To stabilize the single chain Fv immunotoxin and to make it more suitable for clinical development, cysteine residues were engineered into framework regions of the $V_H$ and $V_L$ (Mansfield, E. et al., *Blood,* 90:2020-2026 (1997)) generating the molecule RFB4 (dsFv)-PE38.

RFB4 (dsFv)-PE38 is able to kill leukemic cells from patients and induced complete remissions in mice bearing lymphoma xenografts (Kreitman, R. J. et al., *Clin. Cancer Res.,* 6:1476-1487 (2000); Kreitman, R. J. et al., *Int. J. Cancer,* 81:148-155 (1999)). RFB4 (dsFv)-PE38 (BL22) is currently being evaluated in a phase I clinical trial at the National Cancer Institute in patients with hematological malignancies. Sixteen patients with purine analogue resistant hairy cell leukemia were treated with BL22 and 11 (86%) have achieved complete remissions (Kreitman, R. J. et al., *N. Engl. J. Med.* (2001)).

Because of the clinical benefits obtained with BL22, and because improved binding affinity has been shown to improve selective tumor delivery of scFvs (Adams et al., *Cancer Res.* 58:485-490 (1998)), improving the binding affinity of scFvs and other targeting moieties (such as dsFvs, Fabs, and F(ab')$_2$) of immunoconjugates could improve the efficiency of these agents in delivering effector molecules to malignant B-cells. Improved targeting would likely decrease the dose necessary to achieve complete remission of these cancers.

The factors that influence binding affinity are multifaceted and obtaining mutant scFvs with improved affinity is not trivial. Although antibody-antigen crystal structure can suggest which residues are involved in binding, but atomic resolution structural data are not available for most antibodies. Moreover, even when such data is available it cannot generally be predicted which residues and which mutations will result in an antibody with increased antigen binding activity.

BRIEF SUMMARY OF THE INVENTION

The present invention provides improved antibodies for binding to CD22-expressing cells (a "CD22+" cell), especially cancer cells that express CD22 on their exterior surface (a "CD22+ cancer cell"). In this regard, the invention provides anti-CD22 antibodies with a variable light ($V_L$) chain having the sequence of antibody RFB4 and a variable heavy ($V_H$) chain having the sequence of antibody RFB4, but in which residues 100, 100A and 100B of CDR3 of said $V_H$ chain (as numbered by the Kabat and Wu numbering system) have an amino acid sequence selected from the group consisting of: THW, YNR, TTW, and STY. The antibody can be a full length antibody molecule, but is preferably a single chain Fv ("scFv"), a disulfide stabilized Fv ("dsFv"), an Fab, or an F(ab'). In a particularly preferred form, the antibody is a dsFv. (For convenience of reference, the term "antibody" in the text below refers to full length antibodies and, more preferably, to scFv, dsFv, Fab, or F(ab')).

The invention further provides compositions comprising one of these antibodies conjugated or fused to a therapeutic moiety or a detectable label. The therapeutic moiety can be a cytotoxin, a drug, a radioisotope, or a liposome loaded with a drug or a cytotoxin. In preferred embodiments, the effector moiety is a cytotoxin. The cytotoxin can be selected from the group consisting of ricin A, abrin, ribotoxin, ribonuclease, saporin, calicheamycin, diphtheria toxin or a cytotoxic subunit or mutant thereof, a *Pseudomonas* exotoxin, a cytotoxic portion thereof, a mutated *Pseudomonas* exotoxin, a cytotoxic portion thereof, and botulinum toxins A through F. In preferred forms, the cytotoxin is a *Pseudomonas* exotoxin or cytotoxic fragment thereof, or a mutated *Pseudomonas* exotoxin or a cytotoxic fragment thereof. In particularly preferred forms, the *Pseudomonas* exotoxin is selected from the group consisting of PE35, PE38, PE38KDEL, PE40, PE4E, and PE38QQR. In the most preferred embodiment, the *Pseudomonas* exotoxin is PE38. The compositions may further comprise a pharmaceutically acceptable carrier.

The invention further provides the use of an anti-CD22 antibody with a variable light ($V_L$) chain having the sequence of antibody RFB4 and a variable heavy ($V_H$) chain having the sequence of antibody RFB4, provided that residues 100, 100A and 100B of CDR3 of said $V_H$ chain have an amino acid sequence selected from the group consisting of: THW, YNR, TTW, and STY, for the manufacture of a medicament to inhibit the growth of a CD22+ cancer cell. The antibody can be, for example, a full length antibody, an scFv, dsFv, a Fab, or a F(ab')$_2$. In a particularly preferred form, the antibody is a dsFv. The invention further provides for the use of a composition for the manufacture of a medicament for inhibiting growth of a CD22+ cancer cell, which composition comprises an antibody as just described conjugated or fused to a therapeutic moiety or a detectable label. The therapeutic moiety can be, for example, a cytotoxin, a drug, a radioisotope, or a liposome loaded with a drug or a cytotoxin. In preferred forms, the therapeutic moiety is a cytotoxin. The cytotoxin is preferably selected from the group consisting of ricin A, abrin, ribotoxin, ribonuclease, saporin, calicheamycin, diphtheria toxin or a cytotoxic subunit or mutant thereof, a *Pseudomonas* exotoxin, a cytotoxic portion thereof, a mutated *Pseudomonas* exotoxin, a cytotoxic portion thereof, and botulinum toxins A through F. In preferred uses, the cytotoxin is a *Pseudomonas* exotoxin or cytotoxic fragment thereof, or a mutated *Pseudomonas* exotoxin or a cytotoxic fragment thereof and, in particularly preferred uses, is selected from the group consisting of PE35, PE38, PE38KDEL, PE40, PE4E, and PE38QQR, with PE38 being the most preferred.

In another group of embodiments, the invention provides nucleic acids encoding anti-CD22 antibodies with a variable light ($V_L$) chain having the sequence of antibody RFB4 and a variable heavy ($V_H$) chain having the sequence of antibody RFB4, in which residues 100, 100A and 100B of CDR3 of said $V_H$ chain have an amino acid sequence selected from the group consisting of: THW, YNR, TTW, and STY. The antibody can, for example, be a full-length antibody, or can be selected from the group consisting of an scFv, a dsFv, a Fab, or a F(ab')$_2$. In particularly preferred forms, the antibody is a dsFv. The nucleic acid can further encode a polypeptide which is a therapeutic moiety or a detectable label. The therapeutic moiety can be a drug or a cytotoxin. The cytotoxin can be, for example, a *Pseudomonas* exotoxin or cytotoxic fragment thereof, or a mutated *Pseudomonas* exotoxin or a cytotoxic fragment thereof and is preferably selected from the group consisting of PE35, PE38, PE38KDEL, PE40, PE4E, and PE38QQR. In the most preferred form, the *Pseudomonas* exotoxin is PE38. The invention further provides expression vectors comprising any of the nucleic acids described above operably linked to a promoter.

In yet another group of embodiments, the invention provides methods of inhibiting growth of a CD22+ cancer cell. The methods comprise contacting the cell with an anti-CD22 antibody with a variable light ($V_L$) chain having the sequence of antibody RFB4 and a variable heavy ($V_H$) chain having the sequence of antibody RFB4, provided that residues 100, 100A and 100B of CDR3 of said $V_H$ chain have an amino acid sequence selected from the group consisting of: THW, YNR, TTW, and STY, which antibody is fused or conjugated to a therapeutic moiety, which therapeutic moiety inhibits growth of said cell. The antibody can be an scFv, a dsFv, a Fab, or a F(ab')$_2$. In a particularly preferred form, the antibody is a dsFv. The therapeutic moiety can be, for example, a cytotoxin, a drug, a radioisotope, or a liposome loaded with a drug or a cytotoxin. In preferred forms, the therapeutic moiety is a cytotoxin. The cytotoxin can be, for example, ricin A, abrin, ribotoxin, ribonuclease, saporin, calicheamycin, diphtheria toxin or a cytotoxic subunit or mutant thereof, a *Pseudomonas* exotoxin, a cytotoxic portion thereof, a mutated *Pseudomonas* exotoxin, a cytotoxic portion thereof, and botulinum toxins A through F. In preferred forms, the cytotoxin is a *Pseudomonas* exotoxin or cytotoxic fragment thereof, or a mutated *Pseudomonas* exotoxin or a cytotoxic fragment thereof. In particularly preferred embodiments, the *Pseudomonas* exotoxin is selected from the group consisting of PE35, PE38, PE38KDEL, PE40, PE4E, and PE38QQR. In the most preferred embodiment, the *Pseudomonas* exotoxin is PE38.

The invention further provides methods for detecting the presence of a CD22+ cancer cell in a biological sample, said method comprising contacting cells of said biological sample with an anti-CD22 antibody with a variable light ($V_L$) chain having the sequence of a $V_L$ chain of antibody RFB4 and a variable heavy ($V_H$) chain having the sequence of a $V_H$ chain antibody RFB4, provided that residues 100, 100A and 100B of CDR3 of the $V_H$ chain of said anti-CD22 antibody have an amino acid sequence selected from the group consisting of: THW, YNR, TTW, and STY, said antibody being fused or conjugated to a detectable label; and detecting the presence or absence of said label, wherein detecting the presence of said label indicates the presence of a CD22+ cancer cell in said sample. The antibody can be, for example, selected from the group consisting of an scFv, a dsFv, a Fab, or a F(ab')$_2$. In a particularly preferred form, the antibody is a dsFv.

In another group of embodiments, the invention provides kits for detecting the presence of a CD22+ cancer cell in a biological sample, said kit comprising a container, and an anti-CD22 antibody with a variable light ($V_L$) chain having the sequence of a $V_L$ chain of antibody RFB4 and a variable heavy ($V_H$) chain having the sequence of a $V_H$ chain antibody RFB4, provided that residues 100, 100A and 100B of CDR3 of the $V_H$ chain of said anti-CD22 antibody have an amino acid sequence selected from the group consisting of: THW, YNR, TTW, and STY which antibody is fused or conjugated to a detectable label. In some embodiments, the antibody is selected from the group consisting of an scFv, a dsFv, a Fab, or a F(ab')$_2$.

BRIEF DESCRIPTION OF THE DRAWINGS

FIG. 1 sets forth the nucleotide sequence (SEQ ID NO:3) and amino acid sequence (SEQ ID NO:4) of the variable region of the RFB4 light chain and the nucleotide sequence (SEQ ID NO:1) and amino acid sequence (SEQ ID NO:2) of the variable region of the RFB4 heavy chain.

FIG. 2 is a print out of Entry Number 038145 of the Kabat database showing the amino acid sequence (SEQ NO:4) of the variable region of the RFB4 light chain and the Kabat position numbering corresponding to each amino acid residue.

FIG. 3 is a print out of Entry Number 038146 of the Kabat database showing the amino acid sequence (SEQ NO:2) of the variable region of the RFB4 heavy chain and the Kabat position numbering corresponding to each amino acid residue.

DETAILED DESCRIPTION OF THE INVENTION

Introduction

The present invention provides antibodies and antibody fragments that have increased binding affinity for cancer cells bearing the CD22 antigen compared to the anti-CD22 antibody known in the art as RFB4. Mutated scFvs have been discovered and isolated that have increases in affinity of from 3.5 to 15-fold the affinity of wild-type RFB4. Immunotoxins made with these high affinity variants had a significant increase in cytotoxic activity compared to a like immunotoxin made with wild-type RFB4.

These mutants change the amino acid sequence of the residues at positions 100, 100A, and 100B of CDR3 of the $V_H$ chain of RFB4 from the wild type sequence SSY to THW, YNR, or STY. A single amino acid change, for example, the one amino acid difference between the sequence SSY and STY, reduced the dissociation constant ($K_D$) of a chimeric immunotoxin made with the resulting scFV to 49 kD, compared to the 85 kD of a like immunotoxin using the parental antibody RFB4 sequence. A change of SSY to TTW lowered the kD of the resulting immunotoxin to 24 kD. Even more impressively, the mutation of the residues SSY to YNW improved the affinity of the resulting immunotoxin from the 85 kD of the immunotoxin employing the parental, wild-type RFB4 antibody to 10 kD. And, substituting THW for the wild-type sequence of SSY improved the affinity even more, to 6 kD.

These improved affinities are reflected in improved cytotoxic activity of immunotoxins made by fusing or conjugating the antibodies or fragments thereof which retain antigen recognition ability to a cytotoxin. For example, tests of an exemplar immunotoxin made from combining an scFv having an RFB4 VH CDR3 sequence in which SSY was mutated to STY to a cytotoxin showed that the amount of the immunotoxin needed to inhibit 50% of the protein synthesis (known as the $IC_{50}$ of the immunotoxin) in CD22-expressing cancer cells from patients was reduced by as much as much as 7-fold compared to a like immunotoxin made with the wild-type SSY sequence. Similar tests showed with an immunotoxin made with the THW sequence showed that the THW sequence increased the cytotoxic activity of the immunotoxin to cells of the CD22-bearing cancer chronic lymphocytic leukemia by 50 times. An immunotoxin was also made with a dsFv having the THW sequence and tested for cytotoxicity against cells from patients having chronic lymphocytic leukemia (CLL) or hairy cell leukemia (HCL). The THW dsFv immunotoxin showed 10 to 40 times higher cytotoxicity against CLL cells than did the wild type RFB4 dsFv immunotoxin, and 4 to 7 times higher cytotoxicity against HCL cells than the wild type RFB4 dsFv immunotoxin.

The improved affinity of the improved antibody and antibody fragments provided by the present invention can be incorporated into chimeric immunoconjugates to improve the ability of the chimeric immunoconjugate to target B-cells bearing the CD22 antigen. The immunoconjugates can, for example, bear a detectable label such as a radioisotope or a reporter enzyme. These labeled immunoconjugates be used, for example, in in vitro assays to detect the presence of CD22-expressing cells in a biological sample. Typically, the biological sample will be a blood sample or lymphocytes from a blood sample.

In another set of in vitro uses, the immunoconjugate bears a cytotoxin rather than a detectable label. Such immunotoxins can be used to purge a blood sample or culture of lymphocytes from a patient. The purged sample or culture can then be readministered to the patient to boost the functional whiteblood cell population.

In in vivo uses, immunotoxins made with the antibodies or antibody fragments of the invention can be used to inhibit the growth and proliferation of cancer cells bearing the CD22 antigen. As noted in the Background section, an immunotoxin made with the parental antibody, RFB4, is currently in human clinical trials and, when tested against an exemplar CD22-expressing cancer, caused complete remissions in 86% of the patients. The greater affinity of the antibodies and antibody fragments of the invention compared to the parental antibody, RFB4, and the greater cytotoxicity of the resulting immunotoxins means that smaller amounts of the immunotoxins can be administered, thereby achieving the same therapeutic effect while reducing the chance of side effects.

In preferred embodiments, the antibody is a scFv or a dsFv. Many of the recombinant immunotoxins produced from constructs of scFv are one-third the size of IgG-toxin chemical conjugates and are homogeneous in composition. Elimination of the constant portion of the IgG molecule from the scFv results in faster clearance of the immunotoxin after injection into animals, including primates, and the smaller size of the conjugates improves drug penetration in solid tumors. Together, these properties lessen the side effects associated with the toxic moiety by reducing the time in which the immunotoxin (IT) interacts with non-target tissues and tissues that express very low levels of antigen. Making disulfide stabilized Fvs (dsFvs) from anti-CD22 antibodies is discussed in the co-owned application of FitzGerald et al., International Publication Number WO 98/41641, which describes a recombinant anti-CD22 antibody disulfide stabilized through a cysteine placed at amino acid position 44 of the $V_H$ and a cysteine at amino acid position 100 of the $V_L$, and which is incorporated herein by reference.

These advantages, however, are offset to some degree by the loss of antigen binding affinity that occurs when IgGs are converted to scFvs (Reiter et al., Nature Biotechnol. 14:239-1245 (1996)). Increasing affinity has been shown to improve selective tumor delivery of scFvs (Adams et al., Cancer Res. 58:485-490 (1998)), and is likely to increase their usefulness in tumor imaging and treatment. Therefore, increasing the affinity of scFvs and other targeting moieties (such as dsFvs, Fabs. and F(ab')2 of immunoconjugates is desirable to improve the efficiency of these agents in delivering effector molecules, such as toxins and other therapeutic agents, to their intended targets. The improved affinity of the antibodies of the invention therefore is an important advance in the delivery of toxins, drugs, and other therapeutic agents to cell of CD22-expressing cancers.

In the sections below, the terms used herein are defined for additional clarity. The invention is described in more detail. Finally, the examples demonstrate the construction and testing of exemplary immunotoxins using antibodies in which STY, YNR, TTW, or THW was substituted for the SSY sequence of the RFB4 antibody.

DEFINITIONS

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

"CD22" refers to a lineage-restricted B cell antigen belonging to the Ig superfamily. It is expressed in 60-70% of B cell lymphomas and leukemias and is not present on the cell surface in early stages of B cell development or on stem cells. See, e.g. Vaickus et al., Crit. Rev. Oncol/Hematol. 11:267-297 (1991).

As used herein, the term "anti-CD22" in reference to an antibody, refers to an antibody that specifically binds CD22 and includes reference to an antibody which is generated against CD22. In preferred embodiments, the CD22 is a primate CD22 such as human CD22. In a particularly preferred embodiment, the antibody is generated against human CD22 synthesized by a non-primate mammal after introduction into the animal of cDNA which encodes human CD22.

"RFB4" refers to a mouse IgG1 monoclonal antibody that specifically binds to human CD22. RFB4 is commercially available under the name RFB4 from several sources, such as Southern Biotechnology Associates, Inc. (Birmingham Ala.; Cat. No. 9360-01) and Autogen Bioclear UK Ltd. (Calne, Wilts, UK; Cat. No. AB147). RFB4 is highly specific for cells of the B lineage and has no detectable cross-reactivity with other normal cell types. Li et al., Cell. Immunol. 118:85-99 (1989). The heavy and light chains of RFB4 have been cloned. See, Mansfield et al., Blood 90:2020-2026 (1997), which is incorporated herein by reference. The nucleotide sequence and amino acid sequences of the RFB4 heavy chain are SEQ ID NO:1 and SEQ ID NO:2, respectively. The nucleotide sequence and amino acid sequences of the RFB4 light chain are SEQ ID NO:3 and SEQ ID NO:4, respectively. The sequences are set forth in FIG. 1.

Unless otherwise indicated, references herein to amino acid positions of the RFB4 heavy or light chain refer to the numbering of the amino acids under the "Kabat and Wu" system. See, Kabat, E., et al., SEQUENCES OF PROTEINS OF IMMUNOLOGICAL INTEREST, U.S. Government Printing Office, NIH Publication No. 91-3242 (1991), which is hereby incorporated by reference system. It should be noted that the number accorded to a residue under the Kabat and Wu system does not necessarily correspond to the number that one might obtain for a residue in a given heavy or light chain by counting from the amino terminus of that chain. FIGS. 2 and 3 show the correlation between the sequential numbering of the residues of the RFB4 light and heavy chains and the Kabat and Wu numbering of those residues. For convenience, the "Kabat and Wu" numbering is sometimes referred to herein as "Kabat" numbering.

As used herein, "antibody" includes reference to an immunoglobulin molecule immunologically reactive with a particular antigen, and includes both polyclonal and monoclonal antibodies. The term also includes genetically engineered forms such as chimeric antibodies (e.g., humanized murine antibodies), heteroconjugate antibodies (e.g., bispecific antibodies), recombinant single chain Fv fragments (scFv), and disulfide stabilized (dsFv) Fv fragments (see, co-owned U.S. Pat. No. 5,747,654, which is incorporated herein by reference). The term "antibody" also includes antigen binding forms of antibodies (e.g., Fab', F(ab')$_2$, Fab, Fv and rIgG. See also, Pierce Catalog and Handbook, 1994-1995 (Pierce Chemical Co., Rockford, Ill.); Goldsby et al., eds., Kuby, J., *Immunology*, 4th Ed., W.H. Freeman & Co., New York (2000).

An antibody immunologically reactive with a particular antigen can be generated by recombinant methods such as selection of libraries of recombinant antibodies in phage or similar vectors, see, e.g., Huse, et al., *Science* 246:1275-1281 (1989); Ward, et al., *Nature* 341:544-546 (1989); and Vaughan, et al., *Nature Biotech.* 14:309-314 (1996), or by immunizing an animal with the antigen or with DNA encoding the antigen.

Typically, an immunoglobulin has a heavy and light chain. Each heavy and light chain contains a constant region and a variable region, (the regions are also known as "domains"). Light and heavy chain variable regions contain a "framework" region interrupted by three hypervariable regions, also called "complementarity-determining regions" or "CDRs". The extent of the framework region and CDRs have been defined. See, Kabat and Wu, supra. The sequences of the framework regions of different light or heavy chains are relatively conserved within a species. The framework region of an antibody, that is the combined framework regions of the constituent light and heavy chains, serves to position and align the CDRs in three dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or a "VH" refer to the variable region of an immunoglobulin heavy chain, including an Fv, scFv, dsFv or Fab. References to "$V_L$" or a "VL" refer to the variable region of an immunoglobulin light chain, including of an Fv, scFv, dsFv or Fab The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site.

The term "linker peptide" includes reference to a peptide within an antibody binding fragment (e.g., Fv fragment) which serves to indirectly bond the variable domain of the heavy chain to the variable domain of the light chain.

The term "parental antibody" means any antibody of interest which is to be mutated or varied to obtain antibodies or fragments thereof which bind to the same epitope as the parental antibody, but with higher affinity.

The term "hotspot" means a portion of a nucleotide sequence of a CDR or of a framework region of a variable domain which is a site of particularly high natural variation.

Although CDRs are themselves considered to be regions of hypervariability, it has been learned that mutations are not evenly distributed throughout the CDRs. Particular sites, or hotspots, have been identified as these locations which undergo concentrated mutations. The hotspots are characterized by a number of structural features and sequences. These "hotspot motifs" can be used to identify hotspots. Two consensus sequences motifs which are especially well characterized are the tetranucleotide sequence RGYW and the serine sequence AGY, where R is A or G, Y is C or T, and W is A or T.

A "targeting moiety" is the portion of an immunoconjugate intended to target the immunoconjugate to a cell of interest. Typically, the targeting moiety is an antibody, a scFv, a dsFv, an Fab, or an F(ab')₂.

A "toxic moiety" is the portion of a immunotoxin which renders the immunotoxin cytotoxic to cells of interest.

A "therapeutic moiety" is the portion of an immunoconjugate intended to act as a therapeutic agent.

The term "therapeutic agent" includes any number of compounds currently known or later developed to act as antineoplastics, anti-inflammatories, cytokines, anti-infectives, enzyme activators or inhibitors, allosteric modifiers, antibiotics or other agents administered to induce a desired therapeutic effect in a patient. The therapeutic agent may also be a toxin or a radioisotope, where the therapeutic effect intended is, for example, the killing of a cancer cell.

A "detectable label" means, with respect to an immunoconjugate, a portion of the immunoconjugate which has a property rendering its presence detectable. For example, the immunoconjugate may be labeled with a radioactive isotope which permits cells in which the immunoconjugate is present to be detected in immunohistochemical assays.

The term "effector moiety" means the portion of an immunoconjugate intended to have an effect on a cell targeted by the targeting moiety or to identify the presence of the immunoconjugate. Thus, the effector moiety can be, for example, a therapeutic moiety, a toxin, a radiolabel, or a fluorescent label.

The term "immunoconjugate" includes reference to a covalent linkage of an effector molecule to an antibody. The effector molecule can be an immunotoxin.

The terms "effective amount" or "amount effective to" or "therapeutically effective amount" includes reference to a dosage of a therapeutic agent sufficient to produce a desired result, such as inhibiting cell protein synthesis by at least 50%, or killing the cell.

The term "toxin" includes reference to abrin, ricin, *Pseudomonas* exotoxin (PE), diphtheria toxin (DT), botulinum toxin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

The term "contacting" includes reference to placement in direct physical association.

An "expression plasmid" comprises a nucleotide sequence encoding a molecule or interest, which is operably linked to a promoter.

As used herein, "polypeptide", "peptide" and "protein" are used interchangeably and include reference to a polymer of amino acid residues. The terms apply to amino acid polymers in which one or more amino acid residue is an artificial chemical analogue of a corresponding naturally occurring amino acid, as well as to naturally occurring amino acid polymers. The terms also apply to polymers containing conservative amino acid substitutions such that the protein remains functional.

The term "residue" or "amino acid residue" or "amino acid" includes reference to an amino acid that is incorporated into a protein, polypeptide, or peptide (collectively "peptide"). The amino acid can be a naturally occurring amino acid and, unless otherwise limited, can encompass known analogs of natural amino acids that can function in a similar manner as naturally occurring amino acids.

The amino acids and analogs referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Methionine sulfoxide | Met (O) | — |
| Methionine methylsulfonium | Met (S—Me) | — |
| Norleucine | Nle | — |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "conservative substitution", when describing a protein refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups in Table B each contain amino acids that are conservative substitutions for one another:

TABLE B

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton, *PROTEINS*, W. H. Freeman and Company, New York (1984).

The terms "substantially similar" in the context of a peptide indicates that a peptide comprises a sequence with at least 90%, preferably at least 95% sequence identity to the reference sequence over a comparison window of 10-20 amino acids. Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The phrase "disulfide bond" or "cysteine-cysteine disulfide bond" refers to a covalent interaction between two cysteines in which the sulfur atoms of the cysteines are oxidized to form a disulfide bond. The average bond energy of a disulfide bond is about 60 kcal/mol compared to 1-2 kcal/mol for a hydrogen bond. In the context of this invention, the cysteines which form the disulfide bond are within the framework regions of the single chain antibody and serve to stabilize the conformation of the antibody.

The terms "conjugating," "joining," "bonding" or "linking" refer to making two polypeptides into one contiguous polypeptide molecule. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

As used herein, "recombinant" includes reference to a protein produced using cells that do not have, in their native state, an endogenous copy of the DNA able to express the protein. The cells produce the recombinant protein because they have been genetically altered by the introduction of the appropriate isolated nucleic acid sequence. The term also includes reference to a cell, or nucleic acid, or vector, that has been modified by the introduction of a heterologous nucleic acid or the alteration of a native nucleic acid to a form not native to that cell, or that the cell is derived from a cell so modified. Thus, for example, recombinant cells express genes that are not found within the native (non-recombinant) form of the cell, express mutants of genes that are found within the native form, or express native genes that are otherwise abnormally expressed, underexpressed or not expressed at all.

As used herein, "nucleic acid" or "nucleic acid sequence" includes reference to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof as well as conservative variants, i.e., nucleic acids present in wobble positions of codons and variants that, when translated into a protein, result in a conservative substitution of an amino acid.

As used herein, "encoding" with respect to a specified nucleic acid, includes reference to nucleic acids which comprise the information for translation into the specified protein. The information is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolumn* (*Proc. Nat'l Acad. Sci. USA* 82:2306-2309 (1985), or the ciliate *Macronucleus*, may be used when the nucleic acid is expressed in using the translational machinery of these organisms.

The phrase "fusing in frame" refers to joining two or more nucleic acid sequences which encode polypeptides so that the joined nucleic acid sequence translates into a single chain protein which comprises the original polypeptide chains.

As used herein, "expressed" includes reference to translation of a nucleic acid into a protein. Proteins may be expressed and remain intracellular, become a component of the cell surface membrane or be secreted into the extracellular matrix or medium.

By "host cell" is meant a cell which can support the replication or expression of the expression vector. Host cells may be prokaryotic cells such as *E. coli*, or eukaryotic cells such as yeast, insect, amphibian, or mammalian cells.

The phrase "phage display library" refers to a population of bacteriophage, each of which contains a foreign cDNA recombinantly fused in frame to a surface protein. The phage display the foreign protein encoded by the cDNA on its surface. After replication in a bacterial host, typically *E. coli*, the phage which contain the foreign cDNA of interest are selected by the expression of the foreign protein on the phage surface.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "in vivo" includes reference to inside the body of the organism from which the cell was obtained. "Ex vivo" and "in vitro" means outside the body of the organism from which the cell was obtained.

The phrase "malignant cell" or "malignancy" refers to tumors or tumor cells that are invasive and/or able to undergo metastasis, i.e., a cancerous cell.

As used herein, "mammalian cells" includes reference to cells derived from mammals including humans, rats, mice, guinea pigs, chimpanzees, or macaques. The cells may be cultured in vivo or in vitro.

The term "selectively reactive" refers, with respect to an antigen, the preferential association of an antibody, in whole or part, with a cell or tissue bearing that antigen and not to cells or tissues lacking that antigen. It is, of course, recognized that a certain degree of non-specific interaction may occur between a molecule and a non-target cell or tissue. Nevertheless, selective reactivity, may be distinguished as mediated through specific recognition of the antigen. Although selectively reactive antibodies bind antigen, they may do so with low affinity. On the other hand, specific binding results in a much stronger association between the antibody and cells bearing the antigen than between the bound antibody and cells lacking the antigen. Specific binding typically results in greater than 2-fold, preferably greater than 5-fold, more preferably greater than 10-fold and most preferably greater than 100-fold increase in amount of bound antibody (per unit time) to a cell or tissue bearing CD22 as compared to a cell or tissue lacking CD22. Specific binding to a protein under such conditions requires an antibody that is selected for its specificity for a particular protein. A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, ANTIBODIES, A LABORATORY MANUAL, Cold Spring Harbor Publications, New York (1988), for a description of immunoassay formats and conditions that can be used to determine specific immunoreactivity.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Numbering of Amino Acid Residues in the RFB4 Heavy and Light Chains

The positions of amino acid residues in an antibody heavy chain or light chain are conveniently referred to in the art by standard numbering as set forth in Kabat, E., et al., SEQUENCES OF PROTEINS OF IMMUNOLOGICAL INTEREST, U.S. Government Printing Office, NIH Publication No. 91-3242 (1991). See also, Johnson, G. and Wu, T., Nuc. Acids Res. 29:205-206 (2001). The Kabat et al. database is typically referred to in the art as either "Kabat" or "Kabat and Wu". It is now maintained on-line at http://immuno.bme.nwu.edu/. The heavy and light chains of RFB4 have been cloned. See, Mansfield et al., Blood 90:2020-2026 (1997). The amino acid sequences of the RFB4 $V_L$ and $V_H$ chains and a list of the Kabat numbering of the position of each amino acid residue are set forth in the Kabat database under Entry Numbers 038145 and 038146, respectively. FIG. 2 shows the comparison of the numbering of the amino acids of the RFB4 $V_L$ chain to the corresponding Kabat positions as set forth in Kabat Entry 038145; FIG. 3 shows the same comparison for the amino acids of the RFB4 $V_H$ chain, as set forth in Kabat Entry 038146.

Binding of Antibodies and Immunoassays

A. Binding Affinity of Antibodies

The antibodies of this invention bind to their target antigens with an affinity better than that of the parental RFB4 antibody. The antibodies are anti-CD22 antibodies which bind to an extracellular epitope of CD22. Binding affinity for a target antigen is typically measured or determined by standard antibody-antigen assays, such as competitive assays, saturation assays, or immunoassays such as ELISA or RIA.

Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is <1 µM, preferably <100 nM, and most preferably <0.1 nM. Antibody molecules will typically have a $K_D$ in the lower ranges. $K_D=[Ab-Ag]/[Ab][Ag]$ where [Ab] is the concentration at equilibrium of the antibody, [Ag] is the concentration at equilibrium of the antigen and [Ab-Ag] is the concentration at equilibrium of the antibody-antigen complex. Typically, the binding interactions between antigen and antibody include reversible noncovalent associations such as electrostatic attraction, Van der Waals forces and hydrogen bonds. This method of defining binding specificity applies to single heavy and/or light chains, CDRs, fusion proteins or fragments of heavy and/or light chains, that are specific for CD22 if they bind CD22 alone or in combination.

B. Immunoassays

The antibodies can be detected and/or quantified using any of a number of well recognized immunological binding assays (see, e.g., U.S. Pat. Nos. 4,366,241; 4,376,110; 4,517,288; and 4,837,168). For a review of the general immunoassays, see also METHODS IN CELL BIOLOGY, VOL. 37, Asai, ed. Academic Press, Inc. New York (1993); BASIC AND CLINICAL IMMUNOLOGY 7TH EDITION, Stites & Terr, eds. (1991). Immunological binding assays (or immunoassays) typically utilize a ligand (e.g., CD22) to specifically bind to and often immobilize an antibody. The antibodies employed in immunoassays of the present invention are discussed in greater detail supra.

Immunoassays also often utilize a labeling agent to specifically bind to and label the binding complex formed by the ligand and the antibody. The labeling agent may itself be one of the moieties comprising the antibody/analyte complex, i.e., the anti-CD22 antibody. Alternatively, the labeling agent may be a third moiety, such as another antibody, that specifically binds to the antibody/CD22 protein complex.

In one aspect, a competitive assay is contemplated wherein the labeling agent is a second anti-CD22 antibody bearing a label. The two antibodies then compete for binding to the immobilized CD22. Alternatively, in a non-competitive format, the CD22 antibody lacks a label, but a second antibody specific to antibodies of the species from which the anti-CD22 antibody is derived, e.g., murine, and which binds the anti-CD22 antibody, is labeled.

Other proteins capable of specifically binding immunoglobulin constant regions, such as Protein A or Protein G may also be used as the label agent. These proteins are normal constituents of the cell walls of streptococcal bacteria. They exhibit a strong non-immunogenic reactivity with immunoglobulin constant regions from a variety of species (see, generally Kronval, et al., *J. Immunol.* 111:1401-1406 (1973); and Akerstrom, et al., *J. Immunol.* 135:2589-2542 (1985)).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antibody, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting anti-CD22 antibodies in a sample containing the antibodies generally comprises the steps of contacting the sample with an antibody which specifically reacts, under immunologically reactive conditions, to the CD22/antibody complex.

Production of Immunoconjugates

Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents may include various drugs such as vinblastine, daunomycin and the like, cytotoxins such as native or modified *Pseudomonas* exotoxin or Diphtheria toxin, encapsulating agents, (e.g., liposomes) which themselves contain pharmacological compositions, radioactive agents such as $^{125}I$, $^{32}P$, $^{14}C$, $^{3}H$ and $^{35}S$ and other labels, target moieties and ligands.

The choice of a particular therapeutic agent depends on the particular target molecule or cell and the biological effect is desired to evoke. Thus, for example, the therapeutic agent may be a cytotoxin which is used to bring about the death of a particular target cell. Conversely, where it is merely desired to invoke a non-lethal biological response, the therapeutic agent may be conjugated to a non-lethal pharmacological agent or a liposome containing a non-lethal pharmacological agent.

With the therapeutic agents and antibodies herein provided, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

A. Recombinant Methods

The nucleic acid sequences of the present invention can be prepared by any suitable method including, for example, cloning of appropriate sequences or by direct chemical synthesis by methods such as the phosphotriester method of Narang, et al., *Meth. Enzymol.* 68:90-99 (1979); the phosphodiester method of Brown, et al., *Meth. Enzymol.* 68:109-151 (1979); the diethylphosphoramidite method of Beaucage, et al., *Tetra. Lett.* 22:1859-1862 (1981); the solid phase phosphoramidite triester method described by Beaucage & Caruthers, *Tetra. Letts.* 22(20):1859-1862 (1981), e.g., using an automated synthesizer as described in, for example, Needham-VanDevanter, et al. *Nucl. Acids Res.* 12:6159-6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

In a preferred embodiment, the nucleic acid sequences of this invention are prepared by cloning techniques. Examples of appropriate cloning and sequencing techniques, and instructions sufficient to direct persons of skill through many cloning exercises are found in Sambrook, et al., MOLECULAR CLONING: A LABORATORY MANUAL (2ND ED.), Vols. 1-3, Cold Spring Harbor Laboratory (1989)), Berger and Kimmel (eds.), GUIDE TO MOLECULAR CLONING TECHNIQUES, Academic Press, Inc., San Diego Calif. (1987)), or Ausubel, et al. (eds.), CURRENT PROTOCOLS IN MOLECULAR BIOLOGY, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

Nucleic acids encoding native EM or anti-CD22 antibodies can be modified to form the EM, antibodies, or immunoconjugates of the present invention. Modification by site-directed mutagenesis is well known in the art. Nucleic acids encoding EM or anti-CD22 antibodies can be amplified by in vitro methods. Amplification methods include the polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In a preferred embodiment, immunoconjugates are prepared by inserting the cDNA which encodes an anti-CD22 scFv antibody into a vector which comprises the cDNA encoding the EM. The insertion is made so that the scFv and the EM are read in frame, that is in one continuous polypeptide which contains a functional Fv region and a functional EM region. In a particularly preferred embodiment, cDNA encoding a diphtheria toxin fragment is ligated to a scFv so that the toxin is located at the carboxyl terminus of the scFv. In more preferred embodiments, cDNA encoding PE is ligated to a scFv so that the toxin is located at the amino terminus of the scFv.

Once the nucleic acids encoding an EM, anti-CD22 antibody, or an immunoconjugate of the present invention are isolated and cloned, one may express the desired protein in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eucaryotic cells such as the COS, CHO, HeLa and myeloma cell lines. No attempt to describe in detail the various methods known for the expression of proteins in prokaryotes or eukaryotes will be made. In brief, the expression of natural or synthetic nucleic acids encoding the isolated proteins of the invention will typically be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain transcription and translation terminators, initiation sequences, and promoters useful for regulation of the expression of the DNA encoding the protein. To obtain high level expression of a cloned gene, it is desirable to construct expression cassettes which contain, at the minimum, a strong promoter to direct transcription, a ribosome binding site for translational initiation, and a transcription/translation terminator. For *E. coli* this includes a promoter such as the T7, trp, lac, or lambda promoters, a ribosome binding site and preferably a transcription termination signal. For eukaryotic cells, the control sequences can include a promoter and preferably an enhancer derived from immunoglobulin genes, SV40, cytomegalovirus, and a polyadenylation sequence, and may include splice donor and acceptor sequences. The cassettes of the invention can be transferred into the chosen host cell by well-known methods such as calcium chloride transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

One of skill would recognize that modifications can be made to a nucleic acid encoding a polypeptide of the present invention (i.e., anti-CD22 antibody, PE, or an immunoconjugate formed from their combination) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the immunoconjugates, EM, and antibodies of the present invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. J. Am. Chem. Soc. 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

B. Purification

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal. Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

*Pseudomonas* Exotoxin and Other Toxins

Toxins can be employed with antibodies of the present invention to yield immunotoxins. Exemplary toxins include ricin, abrin, diphtheria toxin and subunits thereof, as well as botulinum toxins A through F. These toxins are readily available from commercial sources (e.g., Sigma Chemical Company, St. Louis, Mo.). Diphtheria toxin is isolated from *Corynebacterium diphtheriae*. Ricin is the lectin RCA60 from *Ricinus communis* (Castor bean). The term also references toxic variants thereof. For example, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543 (1972)). The A chain is responsible for inactivating protein synthesis and killing cells. The B chain binds ricin to cell-surface galactose residues and facilitates transport of the A chain into the cytosol (Olsnes, et al., *Nature* 249:627-631 (1974) and U.S. Pat. No. 3,060,165).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B-chain (abrin-b) binds to D-galactose residues (see, Funatsu, et al., *Agr. Biol. Chem.* 52:1095 (1988); and Olsnes, *Methods Enzymol.* 50:330-335 (1978)).

In preferred embodiments of the present invention, the toxin is *Pseudomonas* exotoxin (PE). The term "*Pseudomonas* exotoxin" as used herein refers to a full-length native (naturally occurring) PE or a PE that has been modified. Such modifications may include, but are not limited to, elimination of domain Ia, various amino acid deletions in domains Ib, II and III, single amino acid substitutions and the addition of one or more sequences at the carboxyl terminus such as KDEL (SEQ ID NO:5) and REDL (SEQ ID NO:6). See Siegall, et al., *J. Biol. Chem.* 264:14256-14261 (1989). In a preferred embodiment, the cytotoxic fragment of PE retains at least 50%, preferably 75%, more preferably at least 90%, and most preferably 95% of the cytotoxicity of native PE. In a most preferred embodiment, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The native PE sequence is provided in commonly assigned U.S. Pat. No. 5,602,095, incorporated herein by reference. The method of action is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall, et al., (1989), supra.

PE employed in the present invention include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE include PE40, PE38, and PE35.

In preferred embodiments, the PE has been modified to reduce or eliminate non-specific cell binding, frequently by deleting domain Ia. as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E")) exhibits greatly diminished non-specific cytotoxicity. This mutant form of PE is sometimes referred to as PE4E.

PE40 is a truncated derivative of PE as previously described in the art. See, Pai, et al., *Proc. Nat'l Acad. Sci. USA* 88:3358-62 (1991); and Kondo, et al., *J. Biol. Chem.* 263: 9470-9475 (1988). PE35 is a 35 kD carboxyl-terminal fragment of PE in which amino acid residues 1-279 have deleted and the molecule commences with a met at position 280 followed by amino acids 281-364 and 381-613 of native PE. PE35 and PE40 are disclosed, for example, in U.S. Pat. Nos. 5,602,095 and 4,892,827.

In some preferred embodiments, the cytotoxic fragment PE38 is employed. PE38 is a truncated PE pro-protein composed of amino acids 253-364 and 381-613 which is activated to its cytotoxic form upon processing within a cell (see e.g., U.S. Pat. No. 5,608,039, and Pastan et al., Biochim. Biophys. Acta 1333:C1-C6 (1997)).

As noted above, some or all of domain 1b may be deleted, and the remaining portions joined by a linker or directly by a peptide bond. Some of the amino portion of domain II may be deleted. And, the C-terminal end may contain the native sequence of residues 609-613 (REDLK (SEQ ID NO:7)), or may contain a variation found to maintain the ability of the construct to translocate into the cytosol, such as REDL (SEQ ID NO:6) or KDEL (SEQ ID NO:5), and repeats of these sequences. See, e.g., U.S. Pat. Nos. 5,854,044; 5,821,238; and 5,602,095 and WO 99/51643. While in preferred embodiments, the PE is PE4E, PE40, or PE38, any form of PE in which non-specific cytotoxicity has been eliminated or reduced to levels in which significant toxicity to non-targeted cells does not occur can be used in the immunotoxins of the present invention so long as it remains capable of translocation and EF-2 ribosylation in a targeted cell.

A. Conservatively Modified Variants of PE

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

The term "conservatively modified variants" applies to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

B. Assaying for Cytotoxicity of PE

*Pseudomonas* exotoxins employed in the invention can be assayed for the desired level of cytotoxicity by assays well known to those of skill in the art. Thus, cytotoxic fragments of PE and conservatively modified variants of such fragments can be readily assayed for cytotoxicity. A large number of candidate PE molecules can be assayed simultaneously for cytotoxicity by methods well known in the art. For example, subgroups of the candidate molecules can be assayed for cytotoxicity. Positively reacting subgroups of the candidate molecules can be continually subdivided and reassayed until the desired cytotoxic fragment(s) is identified. Such methods allow rapid screening of large numbers of cytotoxic fragments or conservative variants of PE.

C. Other Therapeutic Moieties

Antibodies of the present invention can also be used to target any number of different diagnostic or therapeutic compounds to cells expressing CD22 on their surface. Thus, an antibody of the present invention, such as an anti-CD22 scFv, may be attached directly or via a linker to a drug that is to be delivered directly to cells bearing CD22. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-CD22 antibody may be an encapsulation system, such as a liposome or micelle that contains a therapeutic composition such as a drug, a nucleic acid (e.g. an antisense nucleic acid), or another therapeutic moiety that is preferably shielded from direct exposure to the circulatory system. Means of preparing liposomes attached to antibodies are well known to those of skill in the art. See, for example, U.S. Pat. No. 4,957,735; and Connor, et al., *Pharm. Ther.* 28:341-365 (1985).

D. Detectable Labels

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

E. Conjugation to the Antibody

In a non-recombinant embodiment of the invention, effector molecules, e.g., therapeutic, diagnostic, or detection moieties, are linked to the anti-CD22 antibodies of the present invention using any number of means known to those of skill in the art. Both covalent and noncovalent attachment means may be used with anti-CD22 antibodies of the present invention.

The procedure for attaching an effector molecule to an antibody will vary according to the chemical structure of the EM. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules such as those available from Pierce Chemical Company, Rockford Ill.

A "linker", as used herein, is a molecule that is used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages which are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, drugs, toxins, and other agents to antibodies one skilled in the art will be able to determine a suitable method for attaching a given agent to an antibody or other polypeptide.

Pharmaceutical Compositions and Administration

The antibody and/or immunoconjugate compositions of this invention (i.e., PE linked to an anti-CD22 antibody of the invention) are particularly useful for parenteral administration, such as intravenous administration or administration into a body cavity.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp. 315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunotoxins of the present invention are included a variety of disease conditions caused by specific human cells that may be eliminated by the toxic action of the fusion protein. One preferred application for the immunotoxins of the invention is the treatment of malignant cells expressing CD22. Exemplary malignant cells include those of chronic lymphocytic leukemia and hairy cell leukemia.

Diagnostic Kits and In Vitro Uses

In another embodiment, this invention provides for kits for the detection of CD22 or an immunoreactive fragment thereof, (i.e., collectively, a "CD22 protein") in a biological sample. A "biological sample" as used herein is a sample of biological tissue or fluid that contains CD22. Such samples include, but are not limited to, tissue from biopsy, blood, and blood cells (e.g., white cells). Preferably, the cells are lymphocytes. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

Kits will typically comprise an anti-CD22 antibody of the present invention. In some embodiments, the anti-CD22 antibody will be an anti-CD22 Fv fragment, such as a scFv or dsFv fragment.

In addition the kits will typically include instructional materials disclosing means of use of an antibody of the present invention (e.g. for detection of mesothelial cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In one embodiment of the present invention, the diagnostic kit comprises an immunoassay. As described above, although the details of the immunoassays of the present invention may vary with the particular format employed, the method of detecting CD22 in a biological sample generally comprises the steps of contacting the biological sample with an antibody of the present invention which specifically reacts, under immunologically reactive conditions, to CD22. The antibody is allowed to bind to CD22 under immunologically reactive conditions, and the presence of the bound antibody is detected directly or indirectly.

Due to the increased affinity of the antibodies of the invention, the antibodies will be especially useful as diagnostic agents and in in vitro assays to detect the presence of CD22 in biological samples. For example, the antibodies taught herein can be used as the targeting moieties of immunoconjugates in immunohistochemical assays to determine whether a sample contains cells expressing CD22. Detection of CD22 in lymphocytes would indicate either that the patient has a cancer characterized by the presence of CD22-expressing cells, or that a treatment for such a cancer has not yet been successful at eradicating the cancer.

In another set of uses for the invention, immunotoxins targeted by antibodies of the invention can be used to purge targeted cells from a population of cells in a culture. Thus, for example, cells cultured from a patient having a cancer expressing CD22 can be purged of cancer cells by contacting the culture with immunotoxins which use the antibodies of the invention as a targeting moiety.

EXAMPLES

Example 1

The experiments reported in this example demonstrate the creation and use of phage display libraries to select RFB4-Fvs that bind the CD22 antigen of Daudi cells with increased affinity over the wild type RBF4-Fv.

The CDR3 of the variable heavy chain ($V_H$) of RFB4 (Fv) was mutated in an attempt to create Fvs with increased antigen binding affinity. The wild type amino acid sequence of $V_H$CDR3 of RFB4 (Fv) contains 14 amino acids, as shown below in Table 1.

TABLE 1

DNA and amino acid sequences of CDR3 heavy chain RFB4

| 95 | 96 | 97 | 98 | 99 | 100 | 100A | 100B | 100C | 100D | 100E | 100F | 101 | 102 |
|----|----|----|----|----|-----|------|------|------|------|------|------|-----|-----|
| H  | S  | G  | Y  | G | S | S | Y | G | V | L | F | A | Y |
| CAT | AGT | <u>GGC</u> | TAC | <u>GGT</u> | <u>AGT</u> | AGC | TAC | GG<u>G</u> | <u>GTT</u> | TTG | TTT | GCT | TAC |

The mutational hot spots in $V_H$ CDR3 of RFB4 are underlined in the Table. A selected subgroup of the hotspots was targeted for mutagenesis: G99 (GGT), S100 (AGT), S100A (AGC), and Y100B (TAC) were randomly mutated and a library of $1.6 \times 10^5$ clones was produced. The residues mutated are shown in bold in the Table. The numbering of the residues follows the Kabat format.

To create a template for the construction of the library, PCR was used to amplify RFB4-Fv from the plasmid pEM10 [RFB4 (scFv)-PE38KDEL]. The following oligomers, which introduced SfiI and NotI restriction sites into the PCR product, were used for this amplification:

SEQ ID NO. 8:
5'TTCTATGCGGCCCAGCCGCCATGGCCGAAGTGCAGCTGGTGGAGTCT-3'

SEQ ID NO. 9:
5'CGGCACCGGCGCACCTGCGGCCGCCCGTTGATTTCCAGCTTGGTGCC-3'.

The resulting PCR product was digested with SfiI and NotI and inserted into the vector, pCANTAB5E (Pharmacia). The resulting phagemid, pCANTAB5E-RFB4, was then modified by inserting a stop codon (TAA) at position 99 (GGT) using site directed mutagenesis (Quick Change™ site-directed mutagenesis Kit, Stratagene). The final phagemid product, pCANTAB5E-RFB4-1, was used as the template for the introduction of the four amino acid randomizations in the $V_H$CDR3 region.

DNA oligomers twelve nucleotides in length, were designed to generate a library randomizing the four chosen consecutive amino acids. Degenerate oligomers with the sequence NNS were used, where N is any of the four nucleotides, and where S is C or G. The following oligonucleotides were used to create the library:

SEQ ID NO. 10:
5'-CAACGTGAAAAAATTAATTATTCGC

SEQ ID NO. 11:
5'-AGCAAACAAACCCCSNNSNNSNNSNNGTAGCCACTATGTCT

SEQ ID NO. 12:
5'-GCTAAACAACTTTCAACAGTCTATGCGGGCAC

The library was constructed by employing two sequential PCR reactions. In the first PCR, 50 pg of the phagemid template, pCANTAB5E-RFB4-1, was combined with 20 pmol each of DNA oligomers SEQ ID No. 3 and SEQ ID No. 4, mixed with two Ready-To-Go PCR beads (Pharmacia) in a 50 µl volume and cycled using the following profile: 1 cycle at 95° C. for 5 min, followed by 30 cycles at 94° C. for 1 min, 55° C. for 1 min, and 72° C. for 1 min. The PCR reaction generated a 402 base pair product containing the mutations. The product was purified using a Qiagen Quick Spin column and quantitated by visualization on a 1% agarose gel. The purified product was used as primers in a second PCR.

In the second PCR, 2 pmol of product from the first PCR reaction was combined with 20 pmol of the DNA oligomer SEQ ID No. 5, 50 pg of phagemid pCANTAB5E-RFB4-1 template, mixed with two PCR beads in 50 µl volume, and cycled using the profile described above. The reaction generated an 884 base pair insert library. The 884 bp PCR product was digested with SfiI and NotI, purified using a Qiaquick column (Qiagen), and 150 ng was ligated into 250 ng of the phage display vector pCANTAB5E, and desalted. Forty nanograms of the ligation were used to transform *E. coli* TG1. Ten transformations were performed to give a library containing $8 \times 10^5$ clones. The phage library was rescued from the transformed bacteria, as previously described (Beers, R. et al., *Clin. Cancer Res.*, 6:2835-2843 (2000)), titered and stored at 4° C. To test whether the library was properly randomized, 16 clones were sequenced through the mutated region. Each clone had a different DNA sequence, thus indicating that a well randomized library for the selection of scFvs with high affinity for binding of the CD22 antigen had been created.

Phage were rescued from the library and panned on Daudi cells, which have $1 \times 10^5$ CD22 binding sites (Shen, G. L. et al., Int. J. Cancer, 42:792-797 (1988)). Cells ($2 \times 10^7$) were pelleted, resuspended in 10 ml of cold blocking buffer (DPBS+0.5% BSA+5 mM EDTA) and rotated slowly for 90 min at 4° C. The cells were then pelleted and resuspended in 1 ml of cold blocking buffer. Phage ($1 \times 10^{12}$) from the library were added to the cell suspension and the mixture was rotated slowly at 4° C. for 90 min. The cells were washed five times with 10 ml of cold blocking buffer. Bound phage were eluted by resuspending the washed cells in 1.5 ml of ice cold 50 mM HCL and incubating on ice for 10 min. Daudi cells were pelleted and the eluted phage were transferred to a tube containing 200 µl of 1M TRIS pH 8. The eluted phage were titered to determine the number of phage captured. 1.5 ml of the eluted phage were reinfected into *E. coli* and amplified for use in the next round of panning. To avoid possible loss of high affinity Fvs, panning was limited to two rounds only (Beers, R. et al., *Clin. Cancer Res.*, 6:2835-2843 (2000)). A 60-fold enrichment was achieved between round 1 and round 2.

After the second round of panning, phage stocks were prepared from twenty-four individual clones and tested for their ability to bind to Daudi cells by flow cytometry. Single colonies of *E. coli* TG1 containing phagemids selected in the $2^{nd}$ round of panning were grown to $OD_{600}=0.3$ in 15 ml of 2xYT medium supplemented with 2% glucose and ampicillin (100 µg/ml). M13KO7 helper phage ($10^{10}$ PFU) was added to the suspension and cells were incubated for 1 h at 37° C. Following incubation, the mixture was centrifuged, resuspended in 30 ml of 2xYT plus ampicillin (100 µg/ml) and kanamycin (50 µg/ml) and grown 16 h at 37° C. Following growth, the cultures were pelleted and phage were precipitated from the supernatant with PEG/NaCl. After centrifugation, the phage pellets were each resuspended in 1 ml of NTE (100 mM NaCl, 10 mM Tris [pH 7.5] and 1 mM EDTA) and titered.

To determine the binding properties of the 24 phage stocks acquired after the second round of panning, phage were mixed with Daudi cells, reacted with a primary anti-M13 antibody followed by reaction with secondary FITC-labeled antibody and finally, fluorescence was measured by flow cytometry.

$5 \times 10^5$ Daudi cells were incubated with $8 \times 10^8$ phage at room temperature for 60 min, cells were washed two times with blocking buffer (DPBS+0.5% BSA+5 mM EDTA) and 5 µg of mouse anti-M13 antibody (Amersham) was added to each sample. The mixture was incubated at room temperature for 20 min, then washed two times with blocking buffer. A goat-anti-mouse-FITC labeled antibody (Jackson ImmunoResearch) was added and cells were incubated for 20 min at room temperature. Cells were washed two times and analysis was performed in a FACSort flow cytometer (Becton Dickinson). Data were acquired using Cell Quest software. For the competition experiment, $5 \times 10^6$ cells were incubated with $8 \times 10^{10}$ wild-type RFB4 single chain Fv (scFv) phage and with 63 µg of RFB4 immunotoxin (100-fold excess). The sample was processed as for cells incubated with phage only.

Daudi cells incubated without phage generated only a background signal when analysed by flow cytometry. In contrast, the fluorescence intensity signal generated by cells incubated with phage carrying an scFv bearing the wild-type $V_H$CDR3 (GSSY) (SEQ ID NO:13) of RFB4 was significant. Cells that were co-incubated with phage carrying an scFv with the wild-type $V_H$CDR3 (GSSY) (SEQ ID NO:13) of RFB4 and the parental GSSY (SEQ ID NO:13) containing immunotoxin [RFB4 (Fv)-PE38], produced a fluorescence signal similar to that of cells incubated without phage. Thus, phage that carry an scFv bearing the wild-type $V_H$CDR3 (GSSY) (SEQ ID NO:13) of RFB4 bind specifically to the CD22 antigen of Daudi cells.

The fluorescence intensity generated by of Daudi cells that were incubated with phage displaying an scFv with the wild-type $V_H$CDR3 (GSSY) (SEQ ID NO:13) of RFB4 was compared to the fluorescence intensity signal generated by incubation of Daudi cells with any one of three other phage (A, B, and C) selected from the randomized library by panning. The fluorescence intensity generated by incubation of phage A and phage B with Daudi cells was greater than the fluorescence intensity signal generated by Daudi cells incubated with phage carrying an scFv bearing the wild-type $V_H$CDR3 (GSSY) (SEQ ID NO:13) of RFB4. Thus, phage A and B carry scFvs that bind to the CD22 antigen of Daudi cells better than phage carrying an scFv with the wild-type $V_H$CDR3 (GSSY) (SEQ ID NO:13) of RFB4. Cells incubated with phage C had a fluorescence intensity similar to that of cells incubated without phage, suggesting that this mutant did not bind the cells. Phage C was classified as a poor binder and was not analyzed further. Only two out of twenty four phage did not bind to the cells.

Twenty-two of the phage studied behaved like phage A and B. The Fvs of these 22 phage were sequenced using PE™ applied Biosystems Big Dye Terminator Cycle Sequencing Kit. The samples were run and analyzed on a PE Applied Biosystem Model 310 automated sequencer. The amino acid residues of the region mutated in $V_H$CDR3 that were deduced from the DNA sequences are shown below in Table 2.

TABLE 2

Sequences of mutant phage obtained after panning

| 99 | 100 | 100A | 100B | | |
|---|---|---|---|---|---|
| G | S | S | Y | (wild type) | (SEQ ID NO: 13) |
| G | T | H | W | (tested as an immunotoxin) | (SEQ ID NO: 14) |
| G | Y | N | W | (tested as an immunotoxin) | (SEQ ID NO: 15) |
| G | T | T | W | (tested as an immunotoxin) | (SEQ ID NO: 16) |
| G | S | T | Y | (tested as an immunotoxin) | (SEQ ID NO: 17) |
| G | K | N | R | (tested as an immunotoxin and found three times) | (SEQ ID NO: 18) |
| G | S | T | R | (found two times) | (SEQ ID NO: 19) |
| G | H | T | F | | (SEQ ID NO: 20) |
| G | N | R | Y | | (SEQ ID NO: 21) |
| G | T | A | Y | | (SEQ ID NO: 22) |
| G | T | N | Y | | (SEQ ID NO: 23) |
| G | L | H | Y | | (SEQ ID NO: 24) |
| G | F | L | Y | | (SEQ ID NO: 25) |
| G | S | R | Y | | (SEQ ID NO: 26) |
| G | R | N | Y | | (SEQ ID NO: 27) |
| G | V | H | R | | (SEQ ID NO: 28) |
| G | A | L | R | | (SEQ ID NO: 29) |
| G | V | R | A | | (SEQ ID NO: 30) |
| G | T | A | K | | (SEQ ID NO: 31) |
| G | R | T | S | | (SEQ ID NO: 32) |

The amino acid sequences of phage isolated after two rounds of panning is shown. The entire Fv of each phage was sequenced, however, only the sequence of the target region is shown.

The randomized library produced an abundance of mutations that resulted in an apparent increased binding affinity of the $V_H$CDR3 of RBF4 Fv for the CD22 antigen of Daudi cells. Thus, a phage display library of random mutants of the CDR3 region of the $V_H$ of RFB4 was created and used to select RFB4 scFvs with improved binding affinity for the CD22 antigen.

Example 2

The studies reported in this Example demonstrate that incorporation of the mutant scFvs selected in Example 1 into the structure of a chimeric immunotoxin molecule increases the cytotoxic activity of the chimeric immunotoxins toward cultured cells that display the CD22 antigen, thereby inhibiting growth of the cultures.

Immunotoxins from each of the three major 100B substitutions GTTW (SEQ ID NO:16), GYNW (SEQ ID NO:15), GTHW (SEQ ID NO:14), GSTY (SEQ ID NO:17), and GKNR (SEQ ID NO:18) were prepared. ScFvs from selected phagemids were PCR amplified using primers that introduced Nde I and HindIII restrictions sites into the final PCR product. The products of the reaction were purified, digested with Nde I and HindIII and cloned into a T7 expression vector in which the scFv was fused in frame to a truncated version of Pseudomonas exotoxin A (PE38) (Brinkmann, U., Mol. Med. Today, 2:439-446 (1996)). The expression and purification of the resulting recombinant immunotoxins was performed as previously described (Beers, R. et al., Clin. Cancer Res., 6:2835-2843 (2000)).

Each immunotoxin was purified to over 95% homogeneity and eluted as a monomer using TSK gel filtration chromatography. The purified immunotoxins were used in cytotoxicity assays on a panel of six antigen-positive lymphoma cell lines.

Cytotoxicity on cell lines was measured by protein synthesis inhibition assays. Cells were plated in 96-well plates at a concentration of $5 \times 10^4$ cells/well. Immunotoxins, prepared as described above, were serially diluted in phosphate-buffered saline (PBS)/0.2% human serum albumin (HSA) and 20 µl was added to each well. Plates were incubated for 20 hours at 37° C. and then pulsed with 1 µCi/well $^3$H-leucine in 20 µL PBS/0.2% HSA for 2.5 hours at 37° C. Radiolabeled material was captured on filtermats and counted in a Betaplate scintillation counter (Pharmacia, Gaithersburg, Md.). Triplicate sample values were averaged and inhibition of protein synthesis determined by calculating percent incorporation by comparison to control wells without added toxin. The activity of the molecule is defined by its $IC_{50}$, defined as the toxin concentration that reduced incorporation of radioactivity by 50% compared with the cells that were not treated with the toxin. Table 3 shows the $IC_{50}$ values from several experiments.

TABLE 3

Cytotoxic activity ($IC_{50}$) in ng/ml of selected RFB4-PE38 mutants on six different CD22-positive cell lines

| | JD38 | Ca46 | raji | Daudi | namalwa | Ramos |
|---|---|---|---|---|---|---|
| GSSY (WT) (SEQ ID NO: 13) | 2.3 ± 0.5 | 3.1 ± 0.2 | 5.1 ± 0.15 | 8.1 ± 2.3 | 10.6 ± 1.2 | 252 ± 3 |
| GTHW (SEQ ID NO: 14) | 0.2 ± 0.09 | 1.4 ± 0.5 | 1 ± 0.14 | 1.7 ± 0.1 | 2.8 ± 0.4 | 32 ± 3 |
| GYNW (SEQ ID NO: 15) | 0.6 ± 0.1 | 0.8+ | 0.6 ± 0.07 | 2.1 ± 0.5 | 5.6 ± 3.3 | N.D. |
| GTTW (SEQ ID NO: 16) | 0.7 ± 0.03 | 1.7 ± 0.4 | 2.75 ± 0.3 | 2.0 ± 1.2 | 5.3 ± 0.2 | N.D. |
| GSTY (SEQ ID NO: 17) | 1.1+ | 2+ | 4.1+ | 8.5 ± 0.7 | 9.5+ | N.D. |

TABLE 3-continued

Cytotoxic activity (IC$_{50}$) in ng/ml of selected RFB4-PE38 mutants on six different CD22-positive cell lines

|  | JD38 | Ca46 | raji | Daudi | namalwa | Ramos |
|---|---|---|---|---|---|---|
| GKNR (SEQ ID NO: 18) | 5[+] | 6[+] | 10[+] | 55 ± 7 | 25[+] | N.D. |

N.D.: not determined.
[+]Immunotoxin was tested once.
All cell lines were of Burkitt's lymphoma All mutant immunotoxins except GKNR (SEQ ID NO:18) were more cytotoxic to the cell lines bearing the CD22 antigen, than was the immunotoxin that incorporated an scFv with the wild type sequence of the V$_H$CDR3 of RFB4. Since the GKNR (SEQ ID NO:18) mutant was selected because of an apparent increased binding affinity, it would be expected to be more cytotoxic when incorporated into the structure of a chimeric immunotoxin as was the case for the other mutantb scFvs. However, phage display selects for increased expression as well as increased antibody binding affinity. Therefore a dot blot analysis was performed to compare the relative number of wild type (GSSY) (SEQ ID NO:13) scFvs displayed on phage to the number of the GKNR (SEQ ID NO:18) mutant scFvs displayed on phage. The dot blot indicated that the GKNR (SEQ ID NO:18) mutant scFv was overexpressed on the phage. GKNR (SEQ ID NO:18) was not analysed further.

Mutant immunotoxins were not cytotoxic to the CD22 negative cell line HUT-102, indicating that the cytotoxic effect of the immunotoxins is selective to CD22 antigen positive cells.

Thus, by incorporating the mutant scFvs with a higher binding affinity for CD22 antigen into the structure of chimeric RFB4-PE38 immunotoxins, the cytotoxicity of the immunotoxins toward cells bearing the CD22 antigen is enhanced. Therefore, the mutant cytotoxins are more effective at inhibiting growth of the antigen bearing cells than is the immunotoxin with the wild-type (GSSY) (SEQ ID NO:13) V$_H$CDR3 of RBF4.

Example 3

The studies reported in this Example demonstrate that the mutant RFB4-PE38 immunotoxins of Example 2 are more effective at inhibiting the growth of malignant cells taken from patients with advanced lymphocytic disease than is the chimeric immunotoxin bearing the wild-type V$_H$CDR3 of RFB4, RFB4-PE38.

Cytotoxic activity of mutant immunotoxins on malignant cells isolated from patients was measured in blood samples collected from patients as part of approved clinical protocols at the NIH. Patients 1, 2, 3, and 5 have chronic lymphocytic leukemia (CLL). Patient 4 has hairy cell leukemia (HCL). Samples were processed as previously described (Kreitman, R. J. et al., *Clin. Cancer Res.*, 6:1476-1487 (2000)). Briefly, protein synthesis was measured by counting cpm of [$^3$H] leucine incorporated into protein Inhibition of protein synthesis of 50%, defined as being halfway between the level of incorporation of $^3$[H] leucine in the absence of toxin and the level of incorporation of $^3$[H] leucine in the presence of 10 μg/ml of cycloheximide, was determined by capturing radio-labeled material on filter-mats, which were then counted in a Betaplate scintillation counter (Wallac).

Protein synthetic activity of Ficoll purified mononuclear cells from the four patients with chronic lymphocytic leukemia and from the one patient with hairy cell leukemia was determined by incubating the cells with immunotoxins for three days then pulsing with $^3$H leucine for 6-8 h. Each assay was done in triplicate. As can be seen in Table 4, all of the immunotoxins bearing mutant scFvs were more cytotoxic than the chimeric immunotoxin bearing the wild-type RFB4-PE38 with the amino acid sequence GSSY (SEQ ID NO:12) in the V$_H$CDR3 region.

TABLE 4

Cytotoxic activity IC$_{50}$ in ng/ml of mutant immunotoxins on patient cells

|  | Patient 1 | Patient 2 | Patient 3 | Patient 4 | Patient 5 |
|---|---|---|---|---|---|
| GSSY (WT) (SEQ ID NO: 13) | >1000 | 490 ± 70 | 34 ± 5 | 6.7 ± 2.3 | >1000 |
| GTHW (SEQ ID NO: 14) | 29 ± 10 | 22 ± 2 | 1.5 ± 0.4 | <1 | 28 ± 6 |
| GYNW (SEQ ID NO: 14) | 105 ± 48 | 40 ± 5 | 3.4 ± 0.7 | N.D. | 41 ± 2 |
| GTTW (SEQ ID NO: 16) | >1000 | 95 ± 9 | 8.5 ± 3 | 1.5 ± 0.6 | 76 ± 9 |
| GSTY (SEQ ID NO: 17) | N.D. | N.D. | 15 ± 2 | 2.1 ± 0.7 | 129 ± 50 |

Ficoll-purified mononuclear cells from patients were obtained by an approved protocol at the NIH. Cells were incubated with immunotoxins for three days at 37° C. and pulsed with $^3$[H] leucine for 6-8 h; protein synthesis was measured. $IC_{50}$s are expressed in ng/ml, standard deviations are shown. Each assay was done in triplicate. Patients 1, 2, 3, and 5 were diagnosed with CLL, patient 4 with HCL variant. N.D.: not determined.

When tested on cells from patient 2, the chimeric immunotoxin bearing the wild-type GSSY (SEQ ID NO:13) amino acid sequence in the $V_H$CDR3 region of RFB4 had an $IC_{50}$ of 490 ng/ml, the GTHW (SEQ ID NO:14) mutant had an $IC_{50}$ of 22 ng/ml, the GYNW (SEQ ID NO:15) had an $IC_{50}$ of 40 ng/ml, and mutant GTTW (SEQ ID NO:16) mutant had an $IC_{50}$ of 95 ng/ml. Similarly, on samples isolated from patient 5 the chimeric immunotoxin bearing the wild-type GSSY (SEQ ID NO:13) amino acid sequence in the $V_H$CDR3 of RFB4 had an $IC_{50}$ of >1000 ng/ml whereas the immunotoxin with GTHW (SEQ ID NO:14) had an $IC_{50}$ of 28 ng/ml and the GYNW (SEQ ID NO:15) immunotoxin had an $IC_{50}$ of 41 ng/ml and mutant GTTW (SEQ ID NO:16) had an IC50 of 76 ng/ml.

In most of the patients, the parental immunotoxin carrying GSSY (SEQ ID NO:13) amino acid sequence in the $V_H$CDR3 region of RFB4 was not able to inhibit protein synthesis by 50% at the concentrations tested, therefore the $IC_{40}$, the toxin concentration that reduced incorporation of $^3$H-leucine by 40%, was determined instead.

Thus, in every case tested, the chimeric immunotoxins bearing mutant scFvs, were more effective at inhibiting protein synthesis of the leukemic cells than was the chimeric immunotoxin bearing the wild-type scFv.

Example 4

The experiments reported in this example demonstrate that the chimeric RFB4-PE38 immunotoxins, GTHW (SEQ ID NO:14), GYNW (SEQ ID NO:15), GTTW (SEQ ID NO:16), and GSTY (SEQ ID NO:17), which bear the mutant scFvs, bind recombinant CD22 antigen with higher affinity than the chimeric RFB4-PE38 immunotoxin with the wild-type $V_H$CDR3 of RFB4 (GSSY, SEQ ID NO:13).

Binding affinity of the chimeric immunotoxins was determined by plasmon surface resonance (Biacore). First, CD22 recombinant protein was prepared and immobilized it on a CM5 chip. The extracellular domain of CD22 protein was expressed as a fusion to human IgG Fc in transfected 293T cells. The human Fc fragment from plasmid Ret-Fc was PCR amplified using (provided by M. Billaud, Laboratoire de Genetique, Lyon, France) primers which introduced 5' NotI and 3' XbaI restriction sites:

```
                                        (SEQ ID NO: 33)
5'-GAGTGAGTGCGGCCGCGG TGGTCGTCGTGCATCCGT (SEQ ID NO: 34)
5'-TCACTCACTCTAGACGGCCGTCGCACTCATTTAC
```

After digestion with NotI and XbaI, the PCR product was purified and cloned into the NotI and XbaI sites of vector pcDNA1.1 to create plasmid pcDNA1.1-Fc. Next, the extracellular portion of CD22 pcDNA1.1-Fc was fused in-frame with the Fc by amplifying the CD22 extracellular domain from plasmid pRKm22 using the following oligomers:

```
                                        (SEQ ID NO: 35)
5'-GTGAGTGAGAATTCATGCATCTCCTCGGCCCCTG (SEQ ID NO: 36)
5'-TCACTCACTCGCGGCCGCTTCGCCTGCCGATGGTCTC
``` pRKm22 is a plasmid encoding full-length human CD2213 obtained by cloning from a Daudi cDNA Quick clone library (Clontech). The oligomers introduced EcoRI and NotI restriction sites, which were used to clone the purified the PCR product into pcDNA1.1-Fc to create pcDNA1.1-22-Fc. 293T cells were transfected with plasmid pcDNA1.1-22-Fc by standard $CaPO_4$ precipitation.

Binding kinetics of the chimeric immunotoxins were measured using BIAcore 2000 Biosensor. CD22-Fc protein was diluted to 50 μg/ml in amine coupling buffer and immobilized to a BIAcore sensor chip CM5. The chimeric immunotoxins were diluted to 25 μg/ml in HEPES-buffered saline, and on and off rates were measured by injecting 50 μg of immunotoxin over the chip surface at 10 μl/min, and then allowing the bound material to dissociate for 5 min or more. The remaining bound material was removed from CD22 protein by injecting 10 μl of 20 mM phosphoric acid. Each immunotoxin was injected and analyzed at least three times. Binding kinetics were determined using BIA evaluation 2.1 software.

Comparison of the binding profiles of immunotoxins bearing the wild type GSSY (SEQ ID NO:13) amino acid sequence in the $V_H$CDR3 region with the binding profile of the mutant immunotoxins with GTTW (SEQ ID NO:16), GYNW (SEQ ID NO:15) and GTHW (SEQ ID NO:14) in the $V_H$CDR3 region revealed that these three mutant immunotoxins had slower dissociation rates than the GSSY (SEQ ID NO:13) wild-type. In some cases the mutant immunotoxins also had faster association rates compared to wild-type GSSY (SEQ ID NO:13)-containing immunotoxin. In every case however, overall binding affinity of the mutant chimeric immunotoxins exceeded that of the wild-type. Kd was calculated by dividing $K_{off}$ by $K_{on}$. The binding constants, $K_{on}$, $K_{off}$ and Kd are shown below in Table 5.

TABLE 5

Summary of Biacore analysis of RFB4-PE38 mutants

| Immunotoxin | $K_{on}$ ( $M^{-1}s^{-1}$ ) | $K_{off}$ ($s^{-1}$) | KD (nM) |
| --- | --- | --- | --- |
| GSSY (WT) (SEQ ID NO: 13) | 2.08 × 10$^4$ | 1.77 × 10$^{-3}$ | 85 |
| GTHW (SEQ ID NO: 14) | 3.27 × 10$^4$ | 2.07 × 10$^{-4}$ | 6 |
| GYNW (SEQ ID NO: 15) | 1.84 × 10$^4$ | 1.91 × 10$^{-4}$ | 10 |
| GTTW (SEQ ID NO: 16) | 2.62 × 10$^4$ | 6.5 × 10$^{-4}$ | 24 |
| GSTY (SEQ ID NO: 17) | 3.15 × 10$^4$ | 1.55 × 10$^{-3}$ | 49 |

The wild-type, GSSY (SEQ ID NO:13) immunotoxin had a Kd of 85 nM, whereas mutant with highest affinity, GTHW (SEQ ID NO:14), had a Kd of 6 nM, mutant GYNW (SEQ ID NO:15) had a Kd of 10 nM and mutant GTTW (SEQ ID NO:16) had a Kd of 24 nM. Mutant GSTY (SEQ ID NO:17) had a Kd of 49 nM.

Thus, the chimeric immunotoxins bearing mutant scFvs GTHW (SEQ ID NO:14), GYNW (SEQ ID NO:15), GTTW (SEQ ID NO:16), and GSTY (SEQ ID NO:17), bind recombinant CD22 antigen with higher affinity than the chimeric immunotoxin bearing an scFv with the wild-type $V_H$CDR3 of RFB4 through various combinations of faster association rates and slower dissociation rates of the mutant immunotoxins relative to that of the wild-type chimeric immunotoxin Example 5

The studies reported in this Example show that an exemplar chimeric disulfide-stabilized (dsFv) RFB4-PE38 immunotoxin made with the GTHW (SEQ ID NO:14) sequence was strikingly more effective at inhibiting the growth of malignant cells taken from patients with advanced lymphocytic disease than a like chimeric dsFv immunotoxin bearing the wild-type $V_H$CDR3 of RFB4 (GSSY, SEQ ID NO:13).

Disulfide-stabilized Fvs of both sequences were made as previously described for making RFB4(dsFv)-PE38. See, Kreitman et al., Clin Cancer Res 6(4):1476-87 (2000). See also, e.g., U.S. Pat. Nos. 5,747,654, 6,147,203, 6,074,644, and 5,980,895. The immunotoxins were tested against cells taken from seven patients with CLL and against cells taken from two patients with HCL. Cytotoxicity assays were performed as set forth in Example 3, above.

As shown in Table 6, dsFv immunotoxin made with the GTHW (SEQ ID NO:14) sequence was from 10 to 40 times more cytotoxic to cells from patients with CLL than was dsFv immunotoxin made with the wildtype RFB4 sequence. Similarly, the dsFv immunotoxin made with the GTHW (SEQ ID NO:14) sequence was from 4 to 7 times more cytotoxic to cells from patients with HCL than was the dsFv immunotoxin made from the wildtype RFB4 sequence. Thus, dsFv immunotoxins made with the mutated RFB4 sequences of the invention demonstrate strikingly higher cytotoxicity to cells from patients with advanced lymphocytic disease than dsFv immunotoxins made with the wild-type RFB4 sequence.

TABLE 6

Improved Cytotoxic Activity of GTHW (SEQ ID NO: 14) Mutant dsFv Immunotoxin Towards Cells from Patients with CLL or HCL

| | | $IC_{50}$ (ng/ml) | | |
|---|---|---|---|---|
| Pt. No. | Disease | WT | GTHW (SEQ ID NO: 14) | Fold Improvement |
| 1 | CLL | 41 | 1.8 | 23 |
| 2 | CLL | 128 | 11.2 | 11 |
| 3 | CLL | 220 | 22.0 | 10 |
| 4 | CLL | 49 | 4.6 | 11 |
| 5 | CLL | 172 | 6.4 | 27 |
| 6 | CLL | >1000 | 25 | >40 |
| 7 | CLL | 119 | 5.8 | 20 |
| 8 | HCLv | 4 | 0.54 | 7 |
| 9 | HCL | 6 | 1.6 | 4 |

While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited herein are incorporated by reference in their entirety for all purposes to the same extent as if each individual publication or patent document were so individually denoted. Citation of various references in this document is not an admission that any particular reference is considered to be "prior art" to the invention.

What is claimed is:

1. An isolated anti-CD22 antibody with a variable light ($V_L$) chain having the sequence of the $V_L$ chain of antibody RFB4 and a variable heavy ($V_H$) chain having the sequence of the $V_H$ chain of antibody RFB4, provided that residues 100, 100A and 100B of CDR3 of the $V_H$ chain of said anti-CD22 antibody have an amino acid sequence selected from the group consisting of: THW, YNW, TTW, and STY and further provided that residue 100 of the $V_L$ chain of said anti-CD22 antibody is C and residue 44 of the $V_H$ chain of said anti-CD22 antibody is C, as the residues of the $V_L$ and $V_H$ chains are numbered in the column of FIG. 2 or FIG. 3 labeled "Kabat Numbering".

2. An antibody of claim 1, wherein said antibody is selected from the group consisting of an scFv, a dsFv, a Fab, or a F(ab')$_2$.

3. A composition comprising an antibody of claim 1 conjugated or fused to a therapeutic moiety or a detectable label.

4. A composition of claim 3, wherein the therapeutic moiety is selected from the group consisting of a cytotoxin, a drug, a radioisotope, or a liposome loaded with a drug or a cytotoxin.

5. A composition of claim 4, wherein the therapeutic moiety is a cytotoxin.

6. A composition of claim 5, wherein the cytotoxin is selected from the group consisting of ricin A, abrin, ribotoxin, ribonuclease, saporin, calicheamycin, diphtheria toxin or a cytotoxic subunit or mutant thereof, a *Pseudomonas* exotoxin, a cytotoxic portion thereof, a mutated *Pseudomonas* exotoxin, a cytotoxic portion thereof, and botulinum toxins A through F.

7. A composition of claim 6, wherein said cytotoxin is a *Pseudomonas* exotoxin or cytotoxic fragment thereof, or a mutated *Pseudomonas* exotoxin or a cytotoxic fragment thereof.

8. A composition of claim 7, wherein said *Pseudomonas* exotoxin is selected from the group consisting of PE35, PE38, PE38 KDEL, PE40, PE4E, and PE38QQR.

9. A composition of claim 8, wherein the *Pseudomonas* exotoxin is PE38.

10. A composition of claim 3, further comprising a pharmaceutically acceptable carrier.

11. A composition of claim 4, further comprising a pharmaceutically acceptable carrier.

12. A composition of claim 5, further comprising a pharmaceutically acceptable carrier.

13. A composition of claim 6, further comprising a pharmaceutically acceptable carrier.

14. A composition of claim 7, further comprising a pharmaceutically acceptable carrier.

15. A composition of claim 8, further comprising a pharmaceutically acceptable carrier.

16. A composition of claim 9, further comprising a pharmaceutically acceptable carrier.

17. A kit for detecting the presence of a CD22+ cancer cell in a biological sample, said kit comprising:
  (a) a container, and
  (b) an anti-CD22 antibody with a variable light ($V_L$) chain having the sequence of a $V_L$ chain of antibody RFB4 and a variable heavy ($V_H$) chain having the sequence of a $V_H$ chain of antibody RFB4, provided that residues 100, 100A and 100B of CDR3 of the $V_H$ chain of said anti-CD22 antibody have an amino acid sequence selected from the group consisting of: THW, YNW, TTW, and STY and further provided that residue 100 of the $V_L$ chain of said anti-CD22 antibody is C and residue 44 of the $V_H$ chain of said anti-CD22 antibody is C, as the residues of the $V_L$ and $V_H$ chains are numbered in the column of FIG. 2 or FIG. 3 labeled "Kabat Numbering", which antibody is fused or conjugated to a detectable label.

18. A kit of claim 17, wherein said antibody is selected from the group consisting of an scFv, a dsFv, a Fab, or a F(ab')$_2$.

* * * * *

SEQUENCE LISTING

```
<160> NUMBER OF SEQ ID NOS: 38

<210> SEQ ID NO 1
<211> LENGTH: 369
<212> TYPE: DNA
<213> ORGANISM: Artificial Sequence
<220> FEATURE:
<223> OTHER INFORMATION: Description of Artificial Sequence:RFB4 heavy
      chain variable region
<220> FEATURE:
<221> NAME/KEY: CDS
<222> LOCATION: (1)..(369)
<223> OTHER INFORMATION: RBF4 heavy chain variable region

<400> SEQUENCE: 1 gaa gtg cag ctg gtg gag tct ggg gga ggc tta gtg aag cct gga ggg      48
Glu Val Gln Leu Val Glu Ser Gly Gly Gly Leu Val Lys Pro Gly Gly
  1               5                  10                  15 tcc ctg aaa ctc tcc tgt gca gcc tct gga ttc gct ttc agt atc tat      96
Ser Leu Lys Leu Ser Cys Ala Ala Ser Gly Phe Ala Phe Ser Ile Tyr
             20                  25                  30 gac atg tct tgg gtt cgc cag act ccg gag aag agg ctg gag tgg gtc     144
Asp Met Ser Trp Val Arg Gln Thr Pro Glu Lys Arg Leu Glu Trp Val
         35                  40                  45 gca tac att agt agt ggt ggt ggt acc acc tac tat cca gac act gtg     192
Ala Tyr Ile Ser Ser Gly Gly Gly Thr Thr Tyr Tyr Pro Asp Thr Val
     50                  55                  60
```

```
aag ggc cga ttc acc atc tcc aga gac aat gcc aag aac acc ctg tac       240
Lys Gly Arg Phe Thr Ile Ser Arg Asp Asn Ala Lys Asn Thr Leu Tyr
 65                  70                  75                  80 ctg caa atg agc agt ctg aag tct gag gac aca gcc atg tat tac tgt       288
Leu Gln Met Ser Ser Leu Lys Ser Glu Asp Thr Ala Met Tyr Tyr Cys
                 85                  90                  95 gca aga cat agt ggc tac ggt agc agc tac ggg gtt ttg ttt gct tac       336
Ala Arg His Ser Gly Tyr Gly Ser Ser Tyr Gly Val Leu Phe Ala Tyr
            100                 105                 110 tgg ggc caa ggg act ctg gtc act gtc tct gca                           369
Trp Gly Gln Gly Thr Leu Val Thr Val Ser Ala
        115                 120

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence:RFB4 heavy
      chain variable region

<400> SEQUENCE: 2

Glu Val Gln Leu Val Glu Ser Gly Gly Gly Leu Val Lys Pro Gly Gly
 1               5                  10                  15

Ser Leu Lys Leu Ser Cys Ala Ala Ser Gly Phe Ala Phe Ser Ile Tyr
             20                  25                  30

Asp Met Ser Trp Val Arg Gln Thr Pro Glu Lys Arg Leu Glu Trp Val
         35                  40                  45

Ala Tyr Ile Ser Ser Gly Gly Gly Thr Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ala
        115                 120

<210> SEQ ID NO 3
<211> LENGTH: 321
<212> TYPE: DNA
<213> ORGANISM: Artificial Sequence
<220> FEATURE:
<223> OTHER INFORMATION: Description of Artificial Sequence:RFB4 light
      chain variable region
<220> FEATURE:
<221> NAME/KEY: CDS
<222> LOCATION: (1)..(321)
<223> OTHER INFORMATION: RFB4 light chain variable region

<400> SEQUENCE: 3 gat atc cag atg acc cag act aca tcc tcc ctg tct gcc tct ctg gga        48
Asp Ile Gln Met Thr Gln Thr Thr Ser Ser Leu Ser Ala Ser Leu Gly
 1               5                  10                  15 gac aga gtc acc att agt tgc agg gca agt cag gac att agc aat tat        96
Asp Arg Val Thr Ile Ser Cys Arg Ala Ser Gln Asp Ile Ser Asn Tyr
             20                  25                  30 tta aac tgg tat cag cag aaa cca gat gga act gtt aaa ctc ctg atc       144
Leu Asn Trp Tyr Gln Gln Lys Pro Asp Gly Thr Val Lys Leu Leu Ile
         35                  40                  45
```

```
tac tac aca tca ata tta cac tca gga gtc cca tca agg ttc agt ggc      192
Tyr Tyr Thr Ser Ile Leu His Ser Gly Val Pro Ser Arg Phe Ser Gly
         50                  55                  60 agt ggg tct gga aca gat tat tct ctc acc att agc aac ctg gag caa      240
Ser Gly Ser Gly Thr Asp Tyr Ser Leu Thr Ile Ser Asn Leu Glu Gln
 65                  70                  75                  80 gaa gat ttt gcc act tac ttt tgc caa cag ggt aat acg ctt ccg tgg      288
Glu Asp Phe Ala Thr Tyr Phe Cys Gln Gln Gly Asn Thr Leu Pro Trp
                 85                  90                  95 acg ttc ggt gga ggc acc aag ctg gaa atc aaa                          321
Thr Phe Gly Gly Gly Thr Lys Leu Glu Ile Lys
            100                 105
```

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence:RFB4 light
      chain variable region

<400> SEQUENCE: 4

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Ile Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Phe Ala Thr Tyr Phe Cys Gln Gln Gly Asn Thr Leu Pro Trp
                 85                  90                  95

Thr Phe Gly Gly Gly Thr Lys Leu Glu Ile Lys
            100                 105
```

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:carboxyl
      terminus addition to maintain ability of the
      construct to translocate to cytosol

<400> SEQUENCE: 5

Lys Asp Glu Leu
 1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:carboxyl
      terminus addition to maintain ability of the
      construct to translocate to cytosol

<400> SEQUENCE: 6

Arg Glu Asp Leu
 1

-continued

```
<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:C-terminal
      native sequence

<400> SEQUENCE: 7

Arg Glu Asp Leu Lys
 1               5

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence:
      amplification oligomers which introduce SfiI and NotI restriction
      sites

<400> SEQUENCE: 8
ttctatgcgg cccagccgcc atggccgaag tgcagctggt ggagtct                    47

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence:
      amplification oligomers which introduce SfiI and NotI restriction
      sites

<400> SEQUENCE: 9
cggcaccggc gcacctgcgg ccgcccgttg atttccagct tggtgcc                    47

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:DNA
      oligonucleotide used to create library

<400> SEQUENCE: 10
caacgtgaaa aaattaatta ttcgc                                            25

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence:degenerate
      DNA oligonucleotide used to create library
<220> FEATURE:
<221> NAME/KEY: modified_base
<222> LOCATION: (1)..(41)
<223> OTHER INFORMATION: n = g, a, c or t

<400> SEQUENCE: 11
agcaaacaaa ccccsnnsnn snnsnngtag ccactatgtc t                          41

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:DNA
      oligonucleotide used to create library
```

```
<400> SEQUENCE: 12
gctaaacaac tttcaacagt ctatgcgggc ac                                 32

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:wild-type
      (WT) RFB4 V-H CDR3 CD22 target region

<400> SEQUENCE: 13

Gly Ser Ser Tyr
  1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 14

Gly Thr His Trp
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 15

Gly Tyr Asn Trp
  1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 16

Gly Thr Thr Trp
  1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 17

Gly Ser Thr Tyr
  1

<210> SEQ ID NO 18
<211> LENGTH: 4
<212> TYPE: PRT
<213> ORGANISM: Artificial Sequence
```

```
<220> FEATURE:
<223> OTHER INFORMATION: Description of Artificial Sequence:mutated RFB4
      V-H CDR3 CD22 target region

<400> SEQUENCE: 18

Gly Lys Asn Arg
 1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 19

Gly Ser Thr Arg
 1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 20

Gly His Thr Phe
 1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 21

Gly Asn Arg Tyr
 1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 22

Gly Thr Ala Tyr
 1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 23

Gly Thr Asn Tyr
 1
```

-continued

```
<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:mutated RFB4
V-H CDR3 CD22 target region

<400> SEQUENCE: 24

Gly Leu His Tyr
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence:mutated RFB4
V-H CDR3 CD22 target region

<400> SEQUENCE: 25

Gly Phe Leu Tyr
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:mutated RFB4
V-H CDR3 CD22 target region

<400> SEQUENCE: 26

Gly Ser Arg Tyr
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence:mutated RFB4
V-H CDR3 CD22 target region

<400> SEQUENCE: 27

Gly Arg Asn Tyr
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence:mutated RFB4
V-H CDR3 CD22 target region

<400> SEQUENCE: 28

Gly Val His Arg
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:mutated RFB4
V-H CDR3 CD22 target region
```

<400> SEQUENCE: 29

Gly Ala Leu Arg
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 30

Gly Val Arg Ala
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence:mutated RFB4
      V-H CDR3 CD22 target region

<400> SEQUENCE: 31

Gly Thr Ala Lys
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence:mutated RFB4 V-H CDR3 CD22 target region

<400> SEQUENCE: 32

Gly Arg Thr Ser
1

<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence:PCR amplification primers which introduce 5' NotI and 3' XbaI restriction sites

<400> SEQUENCE: 33
gagtgagtgc ggccgcggtg gtcgtcgtgc atccgt 36

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence:PCR amplification primers which introduce 5' NotI and 3' XbaI restriction sites

<400> SEQUENCE: 34
tcactcactc tagacggccg tcgcactcat ttac 34

```
<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence:amplifying
      oligomer

<400> SEQUENCE: 35
gtgagtgaga attcatgcat ctcctcggcc cctg                                34

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence:amplifying
      oligomer

<400> SEQUENCE: 36
tcactcactc gcggccgctt cgcctgccga tggtctc                             37

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence:wild type
      RFB4 variable heavy chain (V-H) CDR3

<400> SEQUENCE: 37
catagtggct acggtagtag ctacggggtt ttgtttgctt ac                       42

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence:wild type
      RFB4 variable heavy chain (V-H) CDR3

<400> SEQUENCE: 38

His Ser Gly Tyr Gly Ser Ser Tyr Gly Val Leu Phe Ala Tyr
  1               5                  10
```